United States Patent
Libbus et al.

(10) Patent No.: US 7,640,057 B2
(45) Date of Patent: Dec. 29, 2009

(54) METHODS OF PROVIDING NEURAL MARKERS FOR SENSED AUTONOMIC NERVOUS SYSTEM ACTIVITY

(75) Inventors: Imad Libbus, St. Paul, MN (US); Andrew P. Kramer, Stillwater, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 720 days.

(21) Appl. No.: 11/113,773

(22) Filed: Apr. 25, 2005

(65) Prior Publication Data

US 2006/0241697 A1    Oct. 26, 2006

(51) Int. Cl.
  *A61B 5/04*  (2006.01)
  *A61N 1/365*  (2006.01)
(52) U.S. Cl. .......................... 607/2; 600/300
(58) Field of Classification Search ......... 600/544–546, 600/300–301, 523; 607/44–46, 48, 60, 62, 607/3
  See application file for complete search history.

(56) References Cited

U.S. PATENT DOCUMENTS

| | | | |
|---|---|---|---|
| 4,201,219 A | 5/1980 | Bozal Gonzalez | |
| 5,111,815 A | 5/1992 | Mower | |
| 5,203,326 A | 4/1993 | Collins | |
| 5,522,854 A | 6/1996 | Ideker et al. | |
| 5,658,318 A | 8/1997 | Stroetmann et al. | |
| 5,974,341 A | 10/1999 | Er et al. | |
| 6,081,743 A | 6/2000 | Carter et al. | |
| 6,132,387 A | 10/2000 | Gozani et al. | |
| 6,224,549 B1 * | 5/2001 | Drongelen | 600/300 |
| 6,400,982 B2 | 6/2002 | Sweeney et al. | |
| 6,535,763 B1 | 3/2003 | Hiebert et al. | |

(Continued)

FOREIGN PATENT DOCUMENTS

EP    0481583 A2    4/1992

(Continued)

OTHER PUBLICATIONS

"International Search Report and Written Opinion for Application No. PCT/US2006/014348, date mailed Aug. 22, 2006", 12 Pages (Continued)

*Primary Examiner*—Carl H Layno
*Assistant Examiner*—Jessica Reidel
(74) *Attorney, Agent, or Firm*—Schwegman, Lundberg & Woessner, P.A.

(57) ABSTRACT

In various method embodiments, a neural activity signal is sensed, a feature from the sensed neural activity signal is extracted, and a neural marker for the extracted feature is created. The neural marker includes information regarding the extracted feature. Various device embodiments comprise a port to receive a neural activity signal, and a feature extractor adapted to receive and process the neural activity signal to produce a neural marker that includes information for the neural activity signal. Various device embodiments comprise a display, a memory adapted to store a neural marker associated with a sensed neural activity signal, and a controller adapted to communicate with the memory and the display to provide a representation of the neural marker on the display.

45 Claims, 14 Drawing Sheets

U.S. PATENT DOCUMENTS

| | | | |
|---|---|---|---|
| 6,583,796 B2 * | 6/2003 | Jamar et al. | 715/804 |
| 6,587,725 B1 * | 7/2003 | Durand et al. | 607/42 |
| 6,658,287 B1 * | 12/2003 | Litt et al. | 600/544 |
| 7,020,521 B1 | 3/2006 | Brewer et al. | |
| 7,225,016 B1 | 5/2007 | Koh | |
| 7,277,761 B2 | 10/2007 | Shelchuk | |
| 2002/0016550 A1 | 2/2002 | Sweeney et al. | |
| 2002/0107553 A1 | 8/2002 | Hill et al. | |
| 2003/0045909 A1 | 3/2003 | Gross et al. | |
| 2003/0055461 A1 | 3/2003 | Girouard et al. | |
| 2003/0060848 A1 | 3/2003 | Kieval et al. | |
| 2003/0195578 A1 | 10/2003 | Perron et al. | |
| 2004/0131998 A1 | 7/2004 | Marom et al. | |
| 2004/0138517 A1 | 7/2004 | Osorio et al. | |
| 2004/0138579 A1 * | 7/2004 | Deadwyler et al. | 600/544 |
| 2004/0215263 A1 | 10/2004 | Virag et al. | |
| 2005/0060001 A1 * | 3/2005 | Singhal et al. | 607/19 |
| 2005/0080348 A1 * | 4/2005 | Stahmann et al. | 600/529 |
| 2005/0085864 A1 | 4/2005 | Schulman et al. | |
| 2005/0096705 A1 | 5/2005 | Pastore et al. | |
| 2005/0143785 A1 | 6/2005 | Libbus | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0261741 A1 | 11/2005 | Libbus et al. | |
| 2006/0106428 A1 | 5/2006 | Libbus et al. | |
| 2006/0106429 A1 | 5/2006 | Libbus et al. | |
| 2006/0135998 A1 | 6/2006 | Libbus et al. | |
| 2006/0167497 A1 * | 7/2006 | Armstrong et al. | 607/2 |
| 2006/0241725 A1 | 10/2006 | Libbus et al. | |

FOREIGN PATENT DOCUMENTS

| | | |
|---|---|---|
| EP | 0688578 A1 | 12/1995 |
| EP | 0770409 A2 | 2/1997 |
| WO | WO-2004036372 A2 | 4/2004 |
| WO | WO-2004043536 A1 | 5/2004 |
| WO | WO-2004068114 A2 | 8/2004 |
| WO | WO-2006055436 A1 | 5/2005 |
| WO | WO-2006055849 A1 | 5/2006 |
| WO | WO-2006115868 A1 | 11/2006 |
| WO | WO-2006115899 A1 | 11/2006 |

OTHER PUBLICATIONS

Bilgutay, A M., "A new concept in the treatment of hypertension utilizing an implantable electronic device: "Baropacer"", *Trans Am Soc Artif Intern Organs.*, 10, (1964), 387-95.

Diedrich, A., "Analysis of raw microneurographic recordings based on wavelet de-noising technique and classification algorithm: wavelet analysis in microneurography", *IEEE Transactions on Biomedical Engineering*, 50 (1), (Jan. 2003), 41-50.

Li, M., "Vagal nerve stimulation markedly improves long-term survival after chronic heart failure in rats", *Circulation*, 109(1), (Jan. 6, 2004), 120-4.

McCraty, Rollin, et al., "The Electricity of Touch: Detection and measurement of cardiac energy exchange between people", *Proceedings of the Fifth Appalachian Conference on Behavioral Neurodynamics*, (1998),1-14.

Sigurdsson, Axel, "The role of neurohormonal activation in chronic heart failure and postmyocardial infarction", *American Heart Journal*, 132 (1 Pt 2 Su), (Jul. 1996), 229-234.

Standford, Vince, "Biosignals Offer Potential for Direct Interfaces and Health Monitoring", *Applications,Pervasive computing*, (Jan.-Mar. 2004), 99-103.

Vanoli, Emilio, "Vagal stimulation and prevention of sudden death in conscious dogs with a healed myocardial infarcation", *Circulation Research*, 68(5), (May 1991), 1471-1481.

\* cited by examiner

| NEUROGRAM | EPISODE | DATE/TIME | NEURAL MARKER LABEL | CORRELATED EVENT |
|---|---|---|---|---|
| ∿∿ | n | | | |
| ∿∿ | n-1 | | | |
| ∿∿ | n-2 | | | |
| | ⋮ | | | |
| | 3 | | | |
| ∿∿ | 2 | | | |
| | 1 | | | |

METHODS OF PROVIDING NEURAL MARKERS FOR SENSED AUTONOMIC NERVOUS SYSTEM ACTIVITY

CROSS REFERENCE TO RELATED APPLICATION

The following commonly assigned U.S. patent applications are related, and are herein incorporated by reference in their entirety: "Method and Apparatus For Simultaneously Presenting Cardiac Neural Signals," Ser. No. 11/114,246, filed on Apr. 25, 2005; "System and Method for Closed-Loop Neural Stimulation," Ser. No. 10/922,319, filed on Nov. 18, 2004; and "Cardiac Rhythm Management Device With Neural Sensor," Ser. No. 10/992,320, filed on Nov. 18, 2004.

Technical Field

This application relates generally to medical devices and, more particularly, to devices to process sensed neural activity.

BACKGROUND

Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various aspects of the present subject matter relate to a method. In various embodiments of the method, a neural activity signal is sensed, a feature from the sensed neural activity signal is extracted, and a neural marker for the extracted feature is created. The neural marker includes information regarding the extracted feature.

Various aspects of the present subject matter relate to a device. In various embodiments, the device comprises a port to receive a neural activity signal, and a feature extractor adapted to receive and process the neural activity signal to produce a neural marker that includes information for the neural activity signal. In various embodiments, the device comprises a display, a memory adapted to store a neural marker associated with a sensed neural activity signal, and a controller adapted to communicate with the memory and the display to provide a representation of the neural marker on the display.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1B:
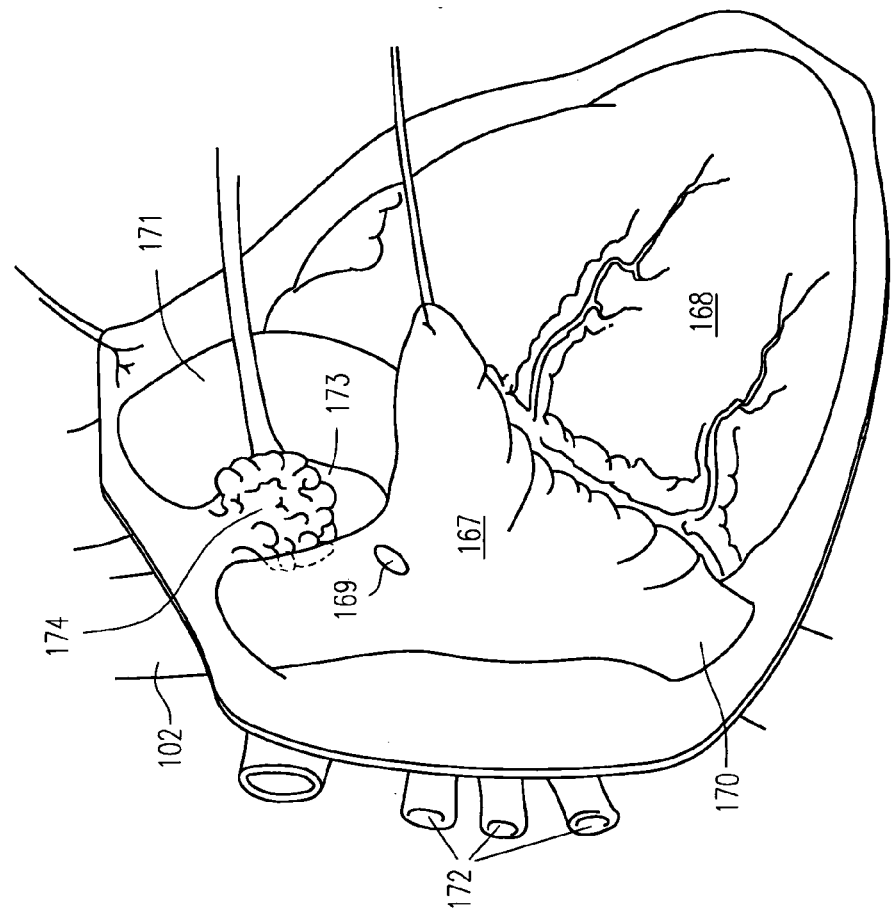
FIGS. 1A-1C illustrate a heart.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to an implantable device that provides neural sensing either with or without neural stimulation and/or neural sensing with or without CRM therapy (such as pacing, defibrillation, CRT or a combinations thereof). The neural sensing system is adapted to identify and mark neural features. These neural markers are capable of being used in applications as provided below.

Various embodiments provide an implantable medical device, with a pulse generator connected to one or more neural leads. The leads can be positioned in a variety of places to sense, and in some embodiments stimulate, efferent and/or afferent neural pathways. Embodiments include electrodes placed proximate to baroreceptors, to other nerve endings or nerve trunks. Some embodiments include a cuff electrode placed around an aortic, carotid or vagus nerve. Some embodiments includes an intravascularly fed lead placed proximal to and adapted to transvascularly stimulate the aortic, carotid or vagus nerve. Various embodiments use an expandable stimulation lead placed in a pulmonary artery in a proximity of a high concentration of baroreceptors. Various embodiments include a transvascular lead placed proximal to one of the cardiac fat pads to stimulate a neural target contained in the cardiac fat pad, or an epicardial lead placed in the cardiac fat pad.

The lead of the implantable medical device is adapted to provide intermittent or continuous neural sensing alone or in combination with neural stimulation and/or CRM therapy. The neural sensing system identifies features from the sensed neural signal, either as neural activity is being monitored and/or recorded, or at a later time from recorded activity. Various embodiments label and time-stamp these features, and various embodiments store and/or display these neural features, with or without the time stamp and label.

Autonomic recordings typically measure nerve traffic density, because individual spike amplitudes are not easily resolved. Thus, detected nerve traffic amplitude includes the amplitude of a rectified/averaged nerve traffic signal. Examples of features identified from the sensed neural signal include absolute amplitude, percent change in amplitude, amplitude above and/or below a given a threshold, absolute frequency, percent change in frequency, and frequency above and/or below a given threshold. Other examples of features include burst pattern, such as duration of activity above a threshold amplitude, timing between the bursts, burst frequency, and the like, and also include a time delay of impulse recordings from a reference time or reference event. Early and late burst can reflect conduction times related to different axon sizes, and can be used to detect activity in different groups of axons. Other features are capable of being extracted from the signal. Some embodiments perform differentiation and/or integration functions on the neural signal to obtain features of the signal. In some embodiments, the sensed neural activity is filtered using wavelet transforms, which are able to provide a time-frequency representation of the sensed neural activity by simultaneously providing time and frequency information. Other filtering techniques can be used.

Some embodiments store and/or display a history of neural markers. For example, the history can be stored in a table, where each entry in a table is a record of a feature of the neural signal. In various embodiments, each neural marker is labeled with information regarding the origination of the neural signal, such as afferent activity, efferent activity, location, etc. Various embodiments use these neural markers to trigger an alert, modify neurostimulation therapy, or modify another therapy, such as CRM therapy or drug therapy. The creation and manipulation of neural markers can be performed by implanted device(s), by external device(s) adapted to receive data from the implanted device through a communication link, or a combination of the implanted and external devices.

The neural markers are capable of providing information useful for therapy. The data recorded with the neural sensing lead is monitored and used to guide therapy, such as neural or CRM therapy. Neural stimulation therapy, for example, can be used to treat several cardiovascular conditions, such as post myocardial infarction remodeling, heart failure and hypertension, for example. Neural stimulation may be particularly effective when applied in conjunction with cardiac pacing, such as cardiac resynchronization therapy (CRT). CRT through biventricular pacing has been shown to improve cardiac function. CRT is enhanced by monitoring and adapting to changes in left ventricular pressure. Various CRM device embodiments use a nerve traffic sensor to monitor nerve traffic and indirectly deduce aortic pressure. Pressure sensors currently suffer from long-term drift, which makes it more difficult to monitor a patient's blood pressure over long periods of time; whereas recording nerve traffic with a neural sensor provides a stable way of monitoring blood pressure.

Some embodiments, for example, use nerve traffic at specific locations as a surrogate for certain physiological parameters, such as arterial pressure or blood gas levels. Various device embodiments record, store, and track pulse pressure data to guide therapy, such as to improve cardiac resynchronization therapy (CRT). Other applications for identified neural markers from sensed neural signals include, but are not limited to, ventricular tachycardia (VT) and ventricular fibrillation (VF) detection, the detection and treatment of sleep apnea and dyspnea, and the detection and treatment of vasovagal syncope.

Baroreceptors and chemoreceptors in the heart, great vessels and lungs transmit cardiac activity through vagal and sympathetic afferent fibers to the central nervous system. In various embodiments, neural sensing is performed using a lead placed in a baroreceptor field such as in the aorta. Various embodiments use a lead placed in or proximate to an efferent nerve pathway such as a cardiac fat pad, and various embodiments use a lead placed around a nerve trunk such as the aortic, carotid, and vagus nerves. According to various embodiments, the targeted nerve traffic corresponds to baroreceptors, and thus are useful to determine blood pressure.

According to various embodiments, the targeted nerve traffic to be sensed corresponds to chemoreceptors, and thus are useful to determine blood gas concentrations.

Physiology

A brief discussion of the physiology related to neurology is provided to assist the reader with understanding this disclosure. This brief discussion introduces the autonomic nervous system, including baroreflex and chemoreceptors, and also introduces cardiac physiology.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The present subject matter senses neural activity and provides neural markers for the sensed activity. Various embodiments detect nerve traffic as a surrogate parameter for another physiologic parameter, such as heart rate, blood pressure and the like. Various embodiments of the present subject matter provide neural stimulation to affect the heart rate, blood pressure, vasodilation and vasoconstriction. The heart rate and force is increased when the sympathetic nervous system is stimulated, and is decreased when the sympathetic nervous system is inhibited (the parasympathetic nervous system is stimulated).

Centrally mediated reflex pathways modulate cardiac rate, contractility and excitability. Baroreceptors and chemoreceptors in the heart, great vessels, and lungs, transmit neural signals reflective of cardiac activity through vagal and afferent fibers to the central nervous system. Thus, physiological parameters, such as systemic arterial pressure, can be determined based on nerve traffic. Such pressure information, for example, provides useful feedback information to guide therapy such as neural therapy or CRM therapy such as CRT.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall). Various embodiments of the present subject matter sense neural signals on the baroreflex pathway.

Some aspects of the present subject matter locally sense specific nerve endings in vessel walls rather than or in addition to afferent and/or efferent nerve trunks. For example, some embodiments sense baroreceptor sites or fields in the pulmonary artery. Some embodiments of the present subject matter involve sensing baroreceptor sites or nerve endings in the aorta, or in the chambers of the heart. Some embodiments of the present subject matter involve sensing efferent pathways such as the fat pads of the heart, and some embodiments of the present subject matter involve sensing an afferent nerve trunk, such as the vagus, carotid and aortic nerves. Various embodiments involve combinations of sensing nerve endings, sensing efferent nerve pathways and sensing afferent nerve pathways. Some embodiments sense nerve trunks using a cuff electrode, and some embodiments sense nerve trunks using an intravascular lead positioned in a blood vessel proximate to the nerve. Examples of afferent nerve trunks include the vagus, aortic and carotid nerves. Examples of efferent nerve trunks include the cardiac branches of the vagus nerve.

Various embodiments of the present subject matter sense nerve traffic corresponding to chemoreceptors. The carotid and aortic bodies provide a concentration of cardiovascular chemoreceptors. The carotid body lies deep to the bifurcation of the common carotid artery or somewhat between the two branches. The carotid body is a small, flattened, oval structure, 2 to 5 mm in diameter, with a characteristic structure composed of epithelioid cells, which are in close relation to capillary sinusoids, and an abundance of nerve fibers. Surrounding the carotid body is a delicate fibrous capsule. It is part of the visceral afferent system of the body, containing chemoreceptor endings that respond to low levels of oxygen in the blood or high levels of carbon dioxide and lowered pH of the blood. It is supplied by nerve fibers from both the glossopharyngeal and vagus nerves. The aortic bodies (glomera, aortica) are chemoreceptors similar to the carotid bodies. Afferent fibers from the aortic bodies run in the right vagus and have cell bodies in the inferior ganglion. The supracardial bodies (aortic paraganglia) are also chemoreceptors with their afferent fibers in the left vagus and cell bodies in the inferior ganglion.

Figure 1A:
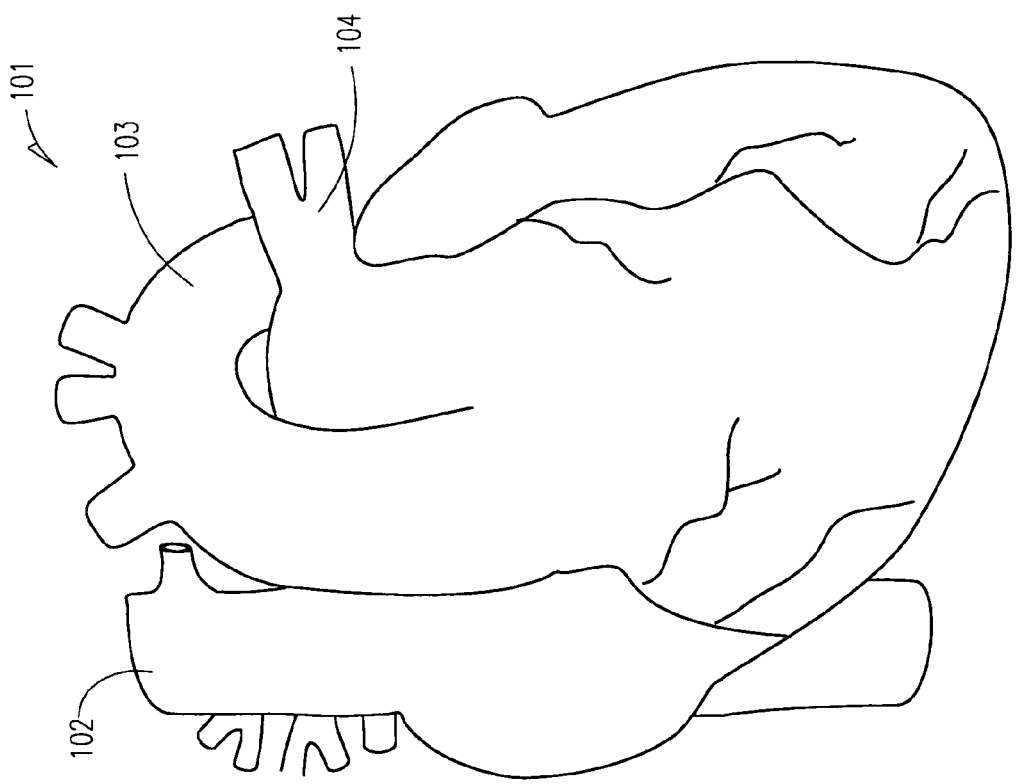
Figure 1C:
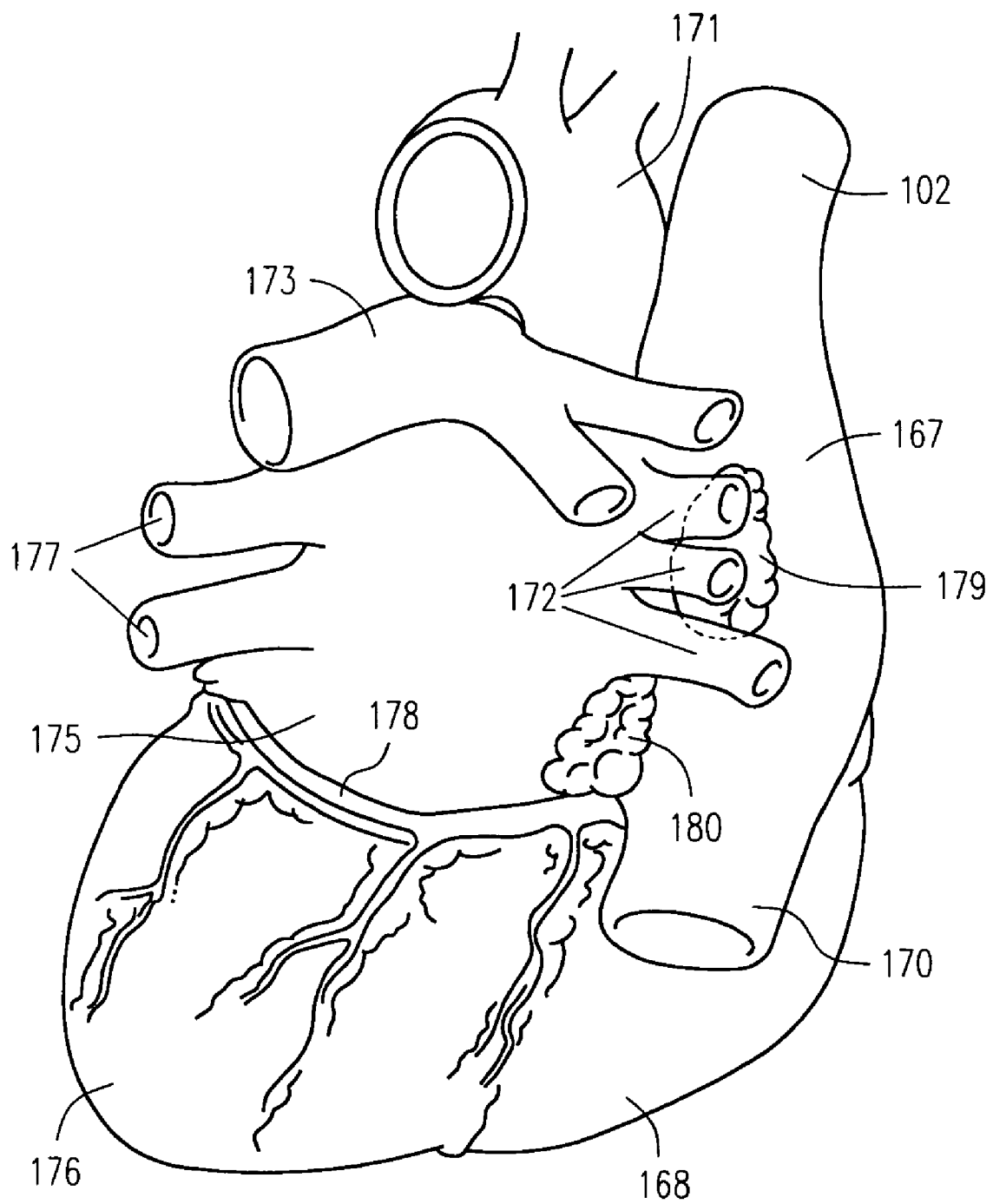

FIGS. 1A-1C illustrate a heart. As illustrated in FIG. 1A, the heart 101 includes a superior vena cava 102, an aortic arch 103, and a pulmonary artery 104. The pulmonary artery 104 includes baroreceptors. According to various embodiments, a lead is intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments sense neural activity by the baroreceptor in the aorta using a lead intravascularly positioned in the pulmonary artery. Some embodiments also stimulate baroreceptors in the aorta. Aspects of the present subject matter provide a relatively noninvasive surgical technique to implant a neural traffic sensor, with or without a baroreceptor stimulator, intravascularly into the pulmonary artery.

FIGS. 1B-1C illustrate the right side and left side of the heart, respectively, and further illustrate cardiac fat pads. FIG. 1B illustrates the right atrium 167, right ventricle 168, sinoatrial node 169, superior vena cava 102, inferior vena cava 170, aorta 171, right pulmonary veins 172, and right pulmonary artery 173. FIG. 1B also illustrates a cardiac fat pad 174 between the superior vena cava and aorta. Autonomic ganglia in the cardiac fat pad 174 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the right pulmonary artery or superior vena cava, for example. FIG. 1C illustrates the left atrium 175, left ventricle 176, right atrium 167, right ventricle 168, superior vena cava 102, inferior vena cava 170, aorta 171, right pulmonary veins 172, left pulmonary vein 177, right pulmonary artery 173, and coronary sinus 178. FIG. 1C also illustrates a cardiac fat pad 179 located proximate to the right cardiac veins and a cardiac fat pad 180 located proximate to the inferior vena cava and left atrium. Autonomic ganglia in the fat pad 179 are stimulated and/or nerve traffic is sensed in some embodiments using an electrode screwed or otherwise inserted into the fat pad 179, and are stimulated and/or nerve traffic is sensed in some embodiments using an intravenously-fed lead proximately positioned to the fat pad in a vessel such as the right pulmonary artery 173 or right pulmonary vein 172, for example. Autonomic ganglia in the cardiac fat pad 180 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the inferior vena cava 170 or coronary sinus or a lead in the left atrium 175, for example.

Figure 2:
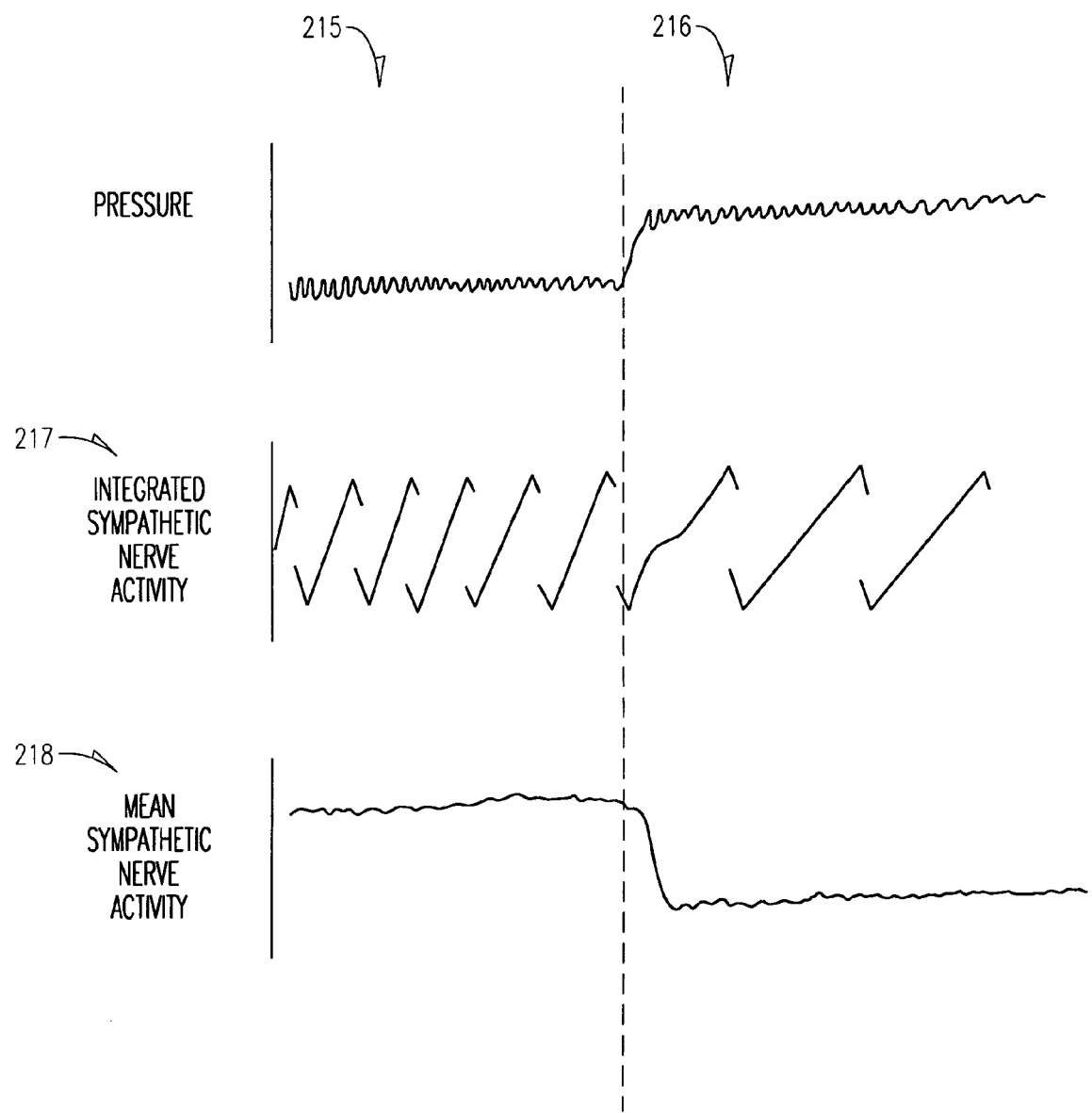
FIG. 2 illustrates an example of a neural response after perturbing a physiologic system.

The present subject matter senses neural activity, and uses information derived from the sensed neural signal to identify physiological conditions or changes. FIG. 2 illustrates an example of a neural response after perturbing a physiologic system. This example is not intended to be exclusive as there are other ways of processing the sensed neural signal to derive information regarding the physiologic conditions or changes. In the illustration, pressure functions as an indicator for a physiologic system. The system is illustrated in a first low pressure condition 215 and a second high pressure condition 216. Nerve activity, illustrated at 217 and 218, changes between the two conditions. The change may be rather transient in nature if the nervous system quickly adapts from the first to the second condition, or may be more sustained if the nervous system does not quickly adapt to the change in conditions. Regardless, an analysis of a sensed nerve traffic signal can extract or otherwise determine features of the signal indicative of the response. In the illustrated example, the waveform 217 associated with an integrated sympathetic nerve activity changes (e.g. change in slope and period of waveform) from the first to the second conditions. Additionally, the waveform 218 associated with a mean sympathetic nerve activity changes (e.g. a first level of nerve activity to a second level of nerve activity) from the first to the second conditions. The integrated sympathetic nerve activity and mean sympathetic nerve activity waveforms are provided as examples of means to extract information from sensed neural activity. Other ways of sensing changes in the neural traffic signals can be used. For example, the neural sensing system identifies important features from the sensed neural signal, either as neural activity is being monitored and/or recorded, or at a later time from recorded activity. Various embodiments label, time-stamp, store and/or display these neural features. Detected nerve traffic amplitude includes the amplitude of a rectified/averaged nerve traffic signal. Examples of features identified from the sensed neural signal include absolute amplitude, percent change in amplitude, amplitude above and/or below a given a threshold, absolute frequency, percent change in frequency, and frequency above and/or below a given threshold. Other examples of features include a time delay of impulse recordings from a reference time or reference event and include a burst pattern, such as duration of activity above a threshold amplitude, timing between the bursts, burst frequency, and the like. Some embodiments perform differentiation and/or integration functions on the neural signal to obtain features of the signal. In some embodiments, the sensed neural activity is filtered using wavelet transforms, which are able to provide a time-frequency representation of the sensed neural activity by simultaneously providing time and frequency information. Other examples of filters include frequency-based filters, such as high-pass, low-pass, band-pass and notch filters. Other examples of filters include filters to rectify a signal, filters to average a signal using moving window averaging, filters to average a signal using logarithmic averaging, and filters to provide signal averaging. Examples of signal averaging filters include includes filters to average repeated signals aligned to an index event such as a stimulation pulse, a sensed R-wave of a cardiac cycle and the like.

System to Process Neural Markers for Sensed Neural Activities

The present subject matter provides systems to provide neural markers for sensed neural activity. The system can include an implantable medical device, an external device, or combinations of implantable and external devices. Some embodiments use the neural markers to control a therapy or therapies. Examples of therapies for which the neural markers provide feedback include neurostimulation therapy, cardiac rhythm management (CRM) therapy, drug therapy, and various combinations thereof.

Figure 3:
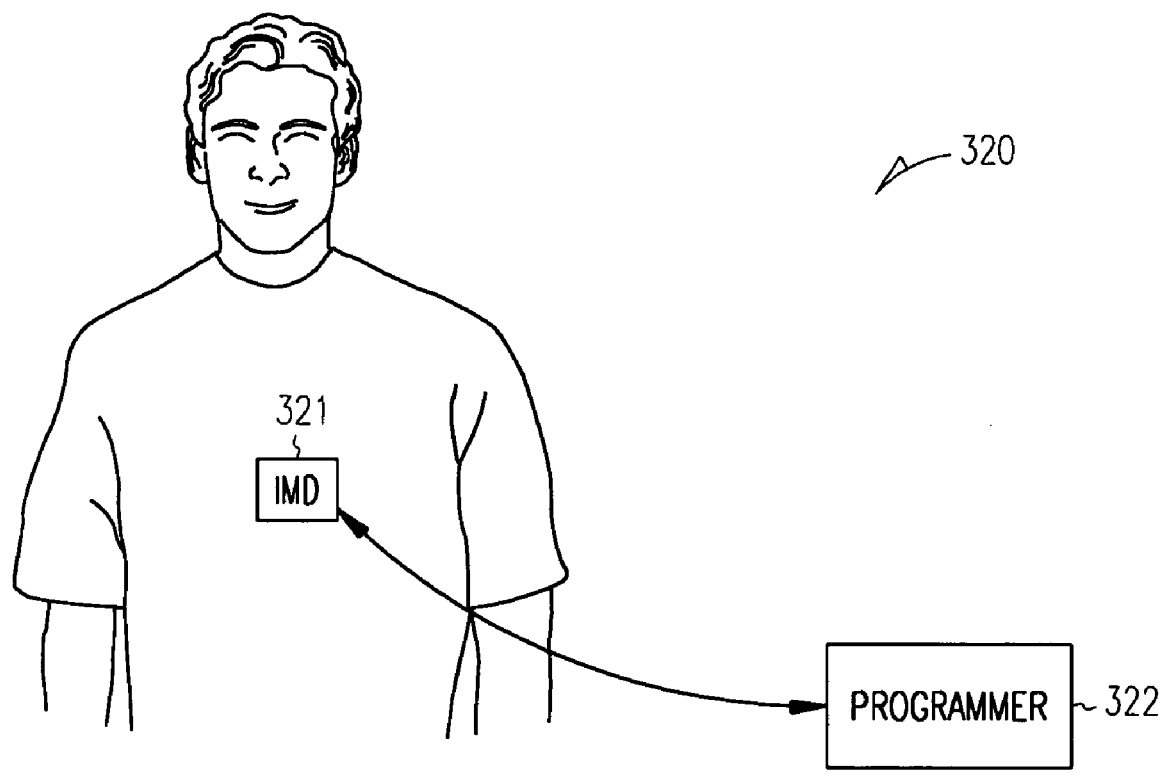
FIG. 3 illustrates a system including an implantable medical device (IMD) and a programmer, according to various embodiments of the present subject matter.

FIG. 3 illustrates a system 320 including an implantable medical device (IMD) 321 and a programmer 322, according to various embodiments of the present subject matter. Various IMD embodiments of the IMD 321 include CRM functions with neural sensing, various embodiments include neural stimulation with neural sensing, various embodiments include drug delivery with neural sensing, and various embodiments include combinations of CRM functions, neural stimulation and drug delivery.

The programmer 322 and the IMD 321 are capable of wirelessly communicating data and instructions. For example, some programmer and IMD embodiments use telemetry coils to wirelessly communicate data and instructions. Thus, the programmer can be used to adjust the programmed therapy provided by the IMD 321, and the IMD can report device data, such as battery and lead resistance, and therapy data, such as sense and stimulation data, to the programmer using radio telemetry, for example.

The IMD 321 includes a sensor to sense ANS activity. Such a sensor can be used to provide nerve traffic feedback in a closed loop control system. In addition to sensing nerve traffic, various IMD embodiments sense surrogate parameters, such as respiration and blood pressure, indicative of ANS activity. Various IMD embodiments include cardiac stimulation capabilities, such as pacing, CRT and defibrillating capabilities. According to various embodiments, the IMD 321 stimulates baroreceptors to provide NS therapy such as AHT therapy. Various IMD embodiments use a lead fed through the right ventricle similar to a cardiac pacemaker lead, and further fed into the pulmonary artery to sense and/or stimulate baroreceptor fields. Other embodiments use other baroreceptor sites or baroreflex pathways or combinations thereof. In some embodiments, the illustrated IMD includes two or more devices capable of communicating with each other via wireless technology; and in some embodiments, the illustrated IMD includes two or more devices capable of communicating with each other via a cable or wire, such as an intravenously fed lead.

Figure 4:
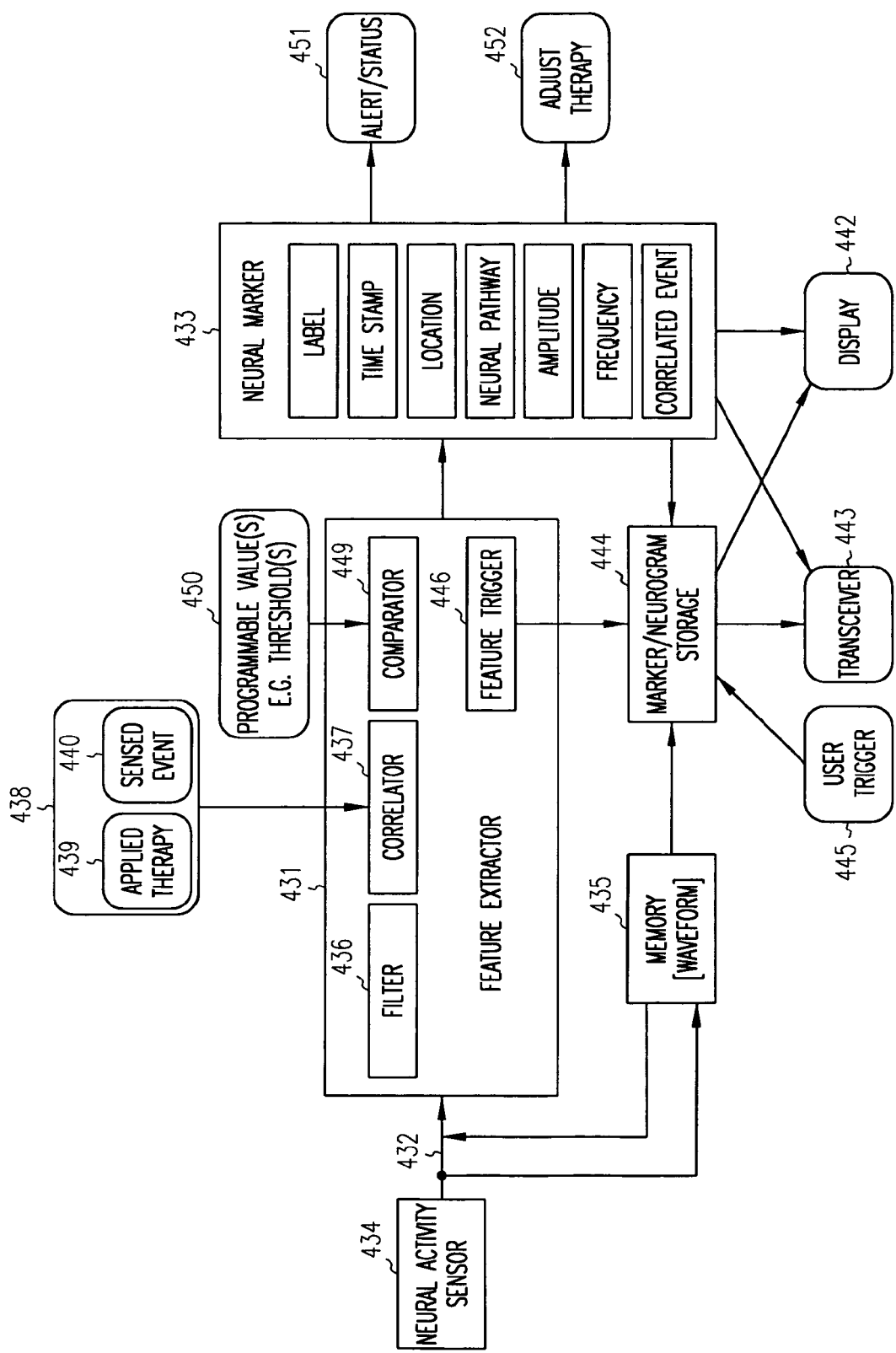
FIG. 4 illustrates a system to provide neural markers for sensed neural activity, according to various embodiments of the present subject matter.

FIG. 4 illustrates a system to provide neural markers for sensed neural activity, according to various embodiments of the present subject matter. The illustration of the system includes a feature extractor 431 connected to a port 432 to receive a neural activity signal via the port 432. The feature extractor processes the neural activity signal into a neural marker 433. The feature extractor can be implemented in an implantable device or an external device. The feature extractor can process the neural activity signal in real time or near real time with respect to a time when the neural activity is sensed by a neural activity sensor 434, such as can occur within the implantable medical device 321 illustrated in FIG.

3, and/or can process a neural activity signal previously sensed and stored in a memory 435, such as can occur within the programmer 322 illustrated in FIG. 3.

The illustrated feature extractor 431 includes a filter 436. An example of a filter includes a wavelet transform filter. Other examples of filters include frequency-based filters, such as high-pass, low-pass, band-pass and notch filters, filters to rectify a signal, filters to average a signal using moving window averaging, filters to average a signal using logarithmic averaging, and filters to provide signal averaging such as filters to average repeated signals aligned to an index event such as a stimulation pulse, a sensed R-wave of a cardiac cycle and the like. Functions of the filter include removing noise from the sensed signal, and transforming the neural activity waveform into a digital signal in preparation for further processing.

The illustrated feature extractor 431 includes a correlator 437. The correlator is used to provide a neural marker for the neural activity signal that corresponds to an event 438. Examples of events include applied therapy events 439 and sensed events 440. Thus, for example, various embodiments of the feature extractor use a correlator 437 to provide a neural marker for the sensed neural activity signal when a therapy, such as when CRM stimulation pulse, a neurostimulation pulse and delivery of a drug dose, is applied. Some embodiments of the feature extractor use a correlator 437 to provide a neural marker for the sensed neural activity signal when an event is sensed, such as a sensed cardiac event, an intrinsic heart rhythm, or a neural signal event detected by the feature extractor, for example.

The illustrated feature extractor 431 includes a comparator 449. The comparator 449 is used to provide a neural marker for the neural activity signal when a feature of the sensed neural signal corresponds to a programmable value 450. Examples of features identified from the sensed neural signal include absolute amplitude, percent change in amplitude, and amplitude above and/or below a given a threshold, where amplitude includes the amplitude of a rectified/averaged nerve traffic signal. Other examples of features include absolute frequency, percent change in frequency, and frequency above and/or below a given threshold. Other examples of features include a time delay of impulse recordings from a reference time or reference event and include a burst pattern, such as duration of activity above a threshold amplitude, timing between the bursts, burst frequency, and the like. As there are a number of features that can be extracted from the neural signal, there are a number of programmable threshold values that can be applied against these extracted features to cause the feature extractor to generate a neural marker.

The illustrated feature extractor 431 receives a neural stimulation signal or waveform at a port 432, either from a sensor or from a memory, extracts features of the signals, and generates a neural marker based on the extracted features of the signal. The neural marker 433 includes information regarding the extracted feature. In various embodiments, the marker includes one or more of a label for the feature, a time stamp, a location of where the neural signal was sensed, an identification for the neural pathway type (such as efferent, afferent), an amplitude for the sensed neural signal, a frequency for the sensed neural signal, and an event, such as an applied therapy or sensed event, correlated with the sensed neural signal. Other information can be provided in the neural marker.

Some system embodiments use the neural marker 433 to provide an alert or a status 451 for the applied therapy. Some embodiments adjust a therapy 452, such as a neurostimulation therapy, CRM therapy and/or drug therapy, based on the neural marker 433. Some embodiments display 442 the neural marker, such as on a display of the programmer 322 of FIG. 3. Some embodiments transmit the neural markers through a transceiver 443 to another device, such as from an implantable medical device to a programmer, as illustrated generally in FIG. 3.

In various embodiments, the neural markers 433 are stored in a memory 444 in preparation for later display or other manipulation. Some embodiments store neural markers in response to a trigger. For example, the neural markers can be stored periodically or intermittently based on preprogrammed time intervals. The illustration includes a user trigger 445 which is used to trigger a storage of a neural marker. Within an implantable device, an example of a user trigger is a reed switch capable of being actuated by placing a magnet outside of a the body proximate to the implantable device. The illustration also includes a trigger 446 in the feature extractor 431, which is used to trigger storage of a neural marker in response to a predetermined extracted feature, such as amplitude, for example. In some embodiments, the memory 444 is adapted to store a neurogram that is associated with the neural marker. The neurogram can be derived from a waveform memory or buffer 435. For example, the recorded neurogram can be for a predetermined or user-selected period of time, and can include waveforms associated with the time immediately before and/or immediately after a neural marker. The neural marker, and neurogram if available, can be displayed 442 or transmitted via transceiver 443 to another device at a later date.

Figures 5, 6:
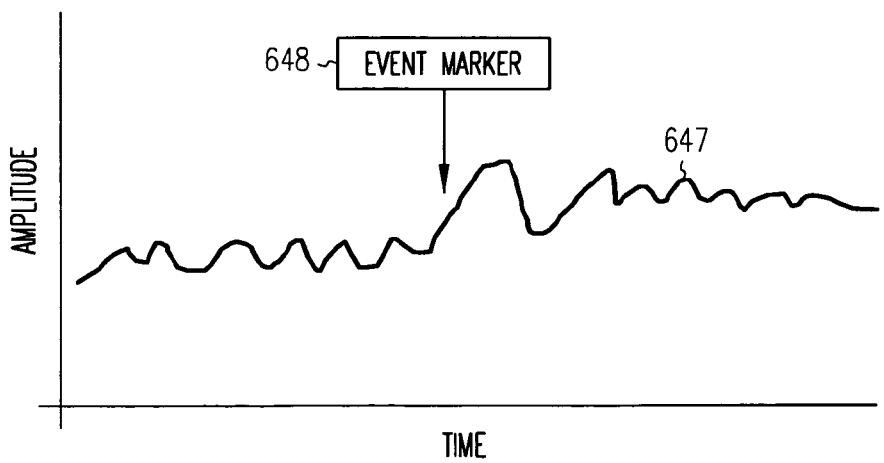
FIG. 5 illustrates a display for a history of neural markers, according to various embodiments.
FIG. 6 illustrates a display with a neurogram and label according to various embodiments, such as may be provided when the icon in the NEUROGRAM column of FIG. 5 is selected.

FIG. 5 illustrates a display for a history of neural markers, according to various embodiments. The illustrated display is included as an example, and is not intended to be exclusive. The illustrated display has a tabular form, with columns labeled NEUROGRAM, EPISODE, DATE/TIME, NEURAL MARKER LABEL, and CORRELATED EVENT. The EPISODE column includes an identifier, such as a number, to uniquely identify the episode. The illustration shows episodes numbered from 1 to n from the bottom to the top of the table. The DATE/TIME column provides information regarding the time associated with the episode, and the LABEL provides an identification for the type of episode associated with the neural marker, based on the extracted features of the neural signal. The CORRELATED EVENT provides an indication of an event, such as an applied therapy or sensed event, that corresponds with the episode. Embodiments of the display include a status indicator (such as color, asterisk, blinking) that provides a viewer with a quick overview of whether or not the detected episode appropriately corresponds to the correlated event. The NEUROGRAM column includes an icon that indicates whether a neurogram is available for the neural marker. In an embodiment, selecting the icon, for example, opens another window to display an associated neurogram, with or without identifiers such as the date/time and/or label. FIG. 6 illustrates a display with a neurogram 647 and label 648 according to various embodiments, such as may be provided when the icon in the NEUROGRAM column of FIG. 5 is selected. Various embodiments display a neurogram for time periods before and/or after the event marker. Additional detail can be linked to each episode and selectively displayed. Such information includes location of the sensed neural signal, the neural pathway type, and the like. The screen display can be used to display any information stored with the neural marker.

Neural Stimulators with Neural Traffic Feedback

Various embodiments include neural stimulation with neural traffic feedback. The lead is adapted to be connected to a device, such as an implantable neural stimulation device or integrated into a CRM device. The device processes the nerve signal with appropriate amplification and filtering for the low amplitude and high noise level associated with the nerve signal. Various embodiments provide a signal processing module that can include a wavelet transformation or other noise reduction algorithm. Recorded nerve traffic is processed with a detection algorithm adapted to identify the features of the signal, such as the pattern and intensity of the nerve traffic. The signal features are used to determine desired neural stimulation parameters, such as duration, frequency and amplitude.

A neural stimulation lead can be placed in a number of appropriate locations. For example, various lead embodiments to stimulate a baroreflex are expandable, and are adapted to be placed in the pulmonary artery in the proximity of a high concentration of baroreceptors. Various lead embodiments are adapted to stimulate nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. Other leads can be placed in other neural stimulation and neural sensing locations to perform baroreflex or other therapy.

The closed-loop neural stimulation can be implemented at a same site or at different sites. In embodiments of a same site implementation, a lead is placed in a baroreceptor field, in a cardiac fat pad, or around or proximate to a nerve trunk (such as the aortic, carotid or vagus nerve). The nerve traffic is detected and monitored with appropriate amplification and filtering characteristics. The pattern and/or intensity of nerve traffic is used to determine neural stimulation parameters, such as duration, frequency, and/or amplitude, at the same site. In embodiments of a different site implementation, two neural leads are placed in different locations, such as one lead in the fat pad and one lead around the vagus nerve, for example. Nerve traffic at one site is used to guide neural stimulation at the second site. Various device embodiments monitor and record autonomic nerve traffic data as part of an APM system.

Various device embodiments include an amplification and filtering circuit adapted to process and monitor nerve traffic. The device includes a signal processing module that includes a noise reduction algorithm such as a wavelet transformation.

Figure 7A:
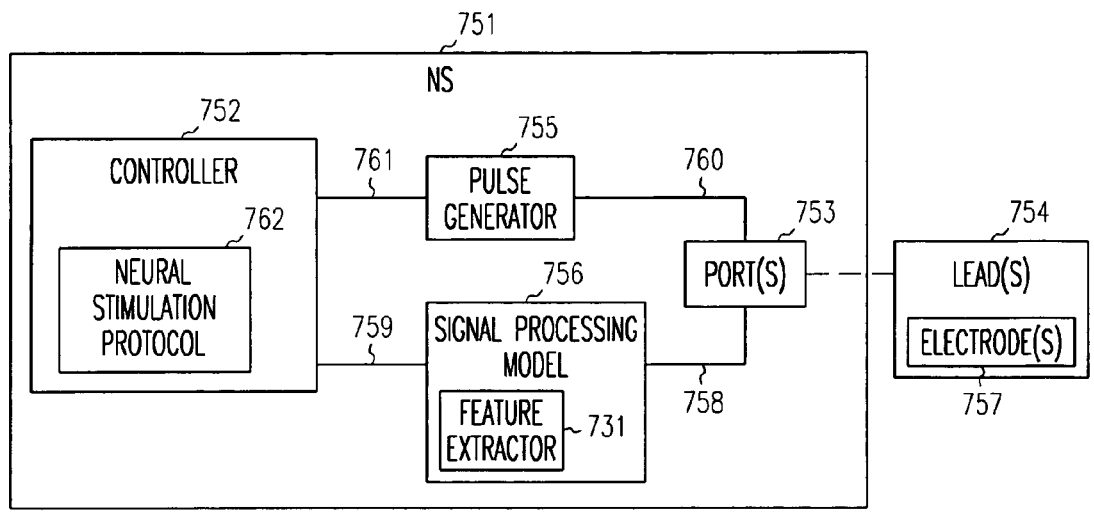
FIGS. 7A-7C illustrate neural stimulators, according to various embodiments of the present subject matter.
Figure 7B:
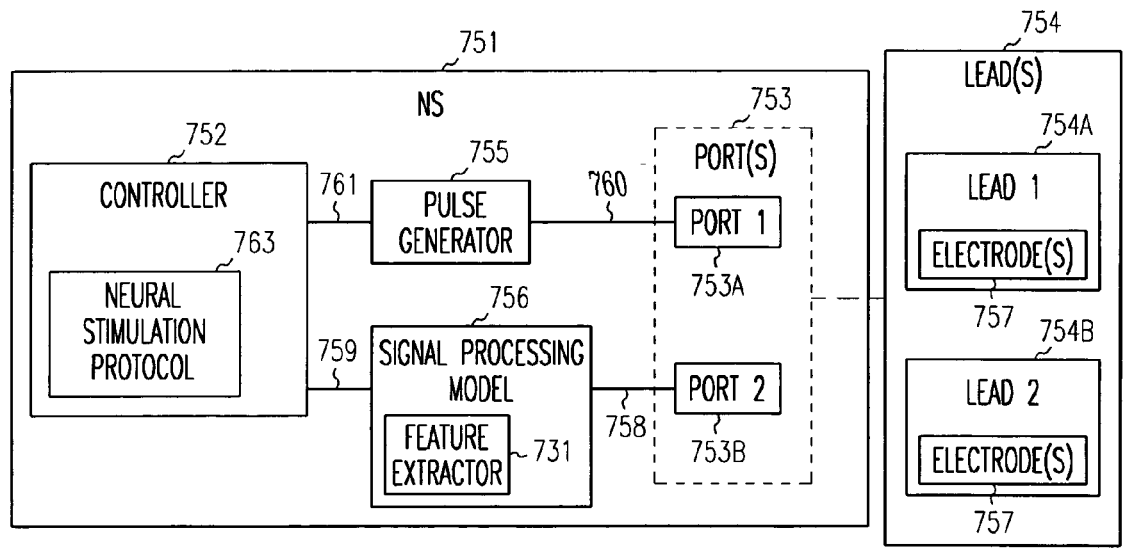
Figure 7C:
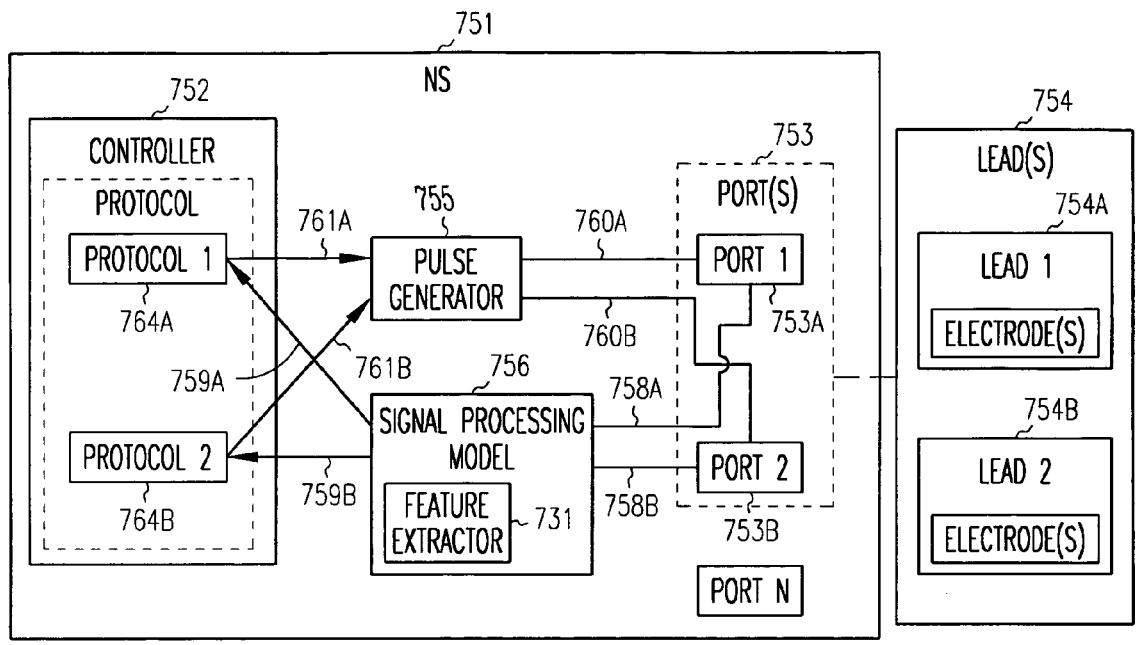

FIGS. 7A-7C illustrate neural stimulators, according to various embodiments of the present subject matter. FIGS. 7A-7C illustrate a few logical arrangements for providing closed-loop neural stimulation based on sensed neural traffic. Other logical arrangements are capable of being implemented.

The neural stimulator device 751 illustrated in FIG. 7A includes a controller 752, at least one port 753 to connect at least one lead 754, a pulse generator 755 connected to the controller and to the port, and a signal processing module 756 connected to the controller and to the port. The at least one lead includes at least one electrode 757 for stimulation and/or sensing. The signal processing module 756 is adapted to receive and process a nerve traffic signal on path 758 from the lead into a signal indicative of the nerve traffic on signal path 759. Embodiments of the signal processing module include a feature extractor 731, such as illustrated at 431 in FIG. 4, for example. The illustrated feature extractor is adapted to receive a signal on 758 and provide a neural marker on 759 for use by the controller. The pulse generator 755 is adapted to provide a neural stimulation signal to the lead on signal path 760 based on a control signal from the controller 752 on path 761. The controller is adapted to implement a neural stimulation protocol 762, which in conjunction with the pulse generator, provides the neural stimulation signal with desired neural stimulation parameters based on the signal indicative of the nerve traffic received from the lead. For example, the duration, frequency and/or amplitude for the neural stimulation signal are capable of being adjusted based on the signal indicative of nerve traffic. The illustrated device is capable of sensing and stimulating using the same lead. Thus, the closed-loop system can be based on sensed nerve traffic at or near the same site where neural stimulation is applied.

The neural stimulator device 751 illustrated in FIG. 7B includes a controller 752, at a first port 753A to connect a first lead 754A and a second port 753B to connect a second lead 754B, a pulse generator 755 connected to the controller and to the first port, and a signal processing module 756 connected to the controller and to the second port. The leads include at least one electrode 757. The signal processing module 756 is adapted to receive and process a nerve traffic signal on path 758 from the second lead 754B into a signal indicative of the nerve traffic on signal path 759. Embodiments of the signal processing module include a feature extractor 731, such as illustrated at 431 in FIG. 4, for example. The illustrated feature extractor is adapted to receive a signal on 758 and provide a neural marker on 759 for use by the controller. The pulse generator 755 is adapted to provide a neural stimulation signal to the lead on signal path 760 based on a control signal from the controller 752 on path 761. The controller is adapted to implement a neural stimulation protocol 763, which in conjunction with the pulse generator, provides the neural stimulation signal with desired neural stimulation parameters to the first lead based on the signal indicative of the nerve traffic received from the second lead. Thus, nerve traffic at one site is capable of being used to guide neural stimulation at another site. For example, the duration, frequency and/or amplitude for the neural stimulation signal are capable of being adjusted based on the signal indicative of nerve traffic.

The neural stimulator device 751 illustrated in FIG. 7C includes a controller 752, a first port 753A to connect a first lead 754A and a second port 753B to connect a second lead 754B, a pulse generator 755 connected to the controller via path 761A and 761B and operably connected to the first and second ports via paths 758A and 758B to perform a desired stimulation, and a signal processing module 756 connected to the controller and operably connected to the first and second ports to provide desired sensing. The leads include at least one electrode. The signal processing module 756 is adapted to receive and process a nerve traffic signal on path 758A from the first lead and on path 758B from the second lead into a signals indicative of the nerve traffic sensed by the first and second leads, respectively. Embodiments of the signal processing module include a feature extractor 731, such as illustrated at 431 in FIG. 4, for example. The illustrated feature extractor is adapted to provide a neural marker for use by the controller. The pulse generator 755 is adapted to provide a neural stimulation signal to the first lead on signal path 760A based on a control signal from the controller 752 on path 761A, and to the second lead on signal path 760B based on a control signal from the controller 752 on path 761B. The controller is adapted to implement a stimulation protocol or protocols 764A and 764B, which in conjunction with the pulse generator, provides the neural stimulation signal with desired neural stimulation parameters to the first lead based on the signal indicative of the nerve traffic received from the second lead, and further provides the neural stimulation with desired neural stimulation parameters to the second lead based on the signal indicative of the nerve traffic received from the first lead. For example, the duration, frequency and/or amplitude for the neural stimulation signal are capable of being adjusted based on the signal indicative of nerve traffic. As illustrated in the FIG. 7C, additional ports (Port N) can be included for use in sensing and/or stimulation.

According to various embodiments, the signal processing module is adapted to provide a signal or signals indicative of a nerve traffic pattern and/or nerve traffic intensity as an indication of the nerve traffic. According to various embodiments, the signal processing module is adapted to implement noise reduction algorithm, such as a wavelet transformation, to identify features of a nerve traffic signal that is characterized by a low amplitude and high noise level. According to various embodiments, the signal processing module includes an amplifier, such as an amplifier with a gain within a range of approximately 1,000; to approximately 99,000. According to various embodiments, the signal processing module includes a bandpass filter, such as a filter to pass frequencies in a range from approximately 30 Hz to approximately 3,000 Hz.

Figure 8:
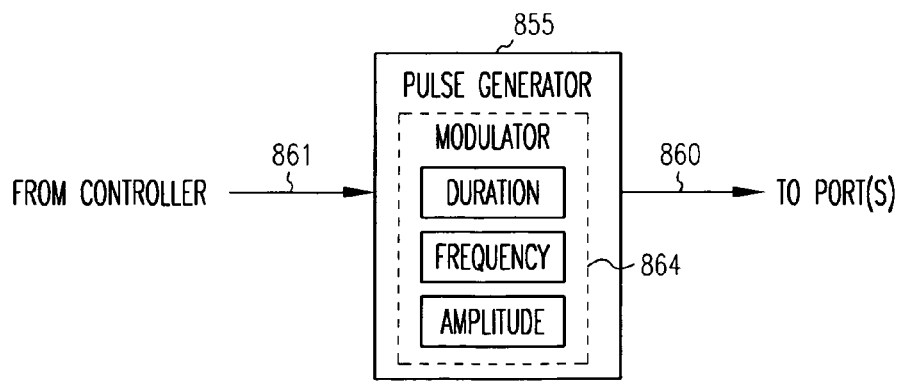
FIG. 8 illustrates a pulse generator, such as shown in the neural stimulators of FIGS. 7A-7C, according to various embodiments of the present subject matter.

FIG. 8 illustrates a pulse generator, such as shown in the neural stimulators of FIGS. 7A-7C, according to various embodiments of the present subject matter. The illustrated pulse generator 855 is adapted to receive a control signal via path 861 from a controller and to provide a neural stimulation signal via path 860 to lead(s) via port(s). The illustrated pulse generator includes a modulator 864 that is responsive to the control signal from the controller to change one or more parameters of the stimulation signal such as the duration, frequency and/or amplitude of the stimulation signal.

Figure 9:
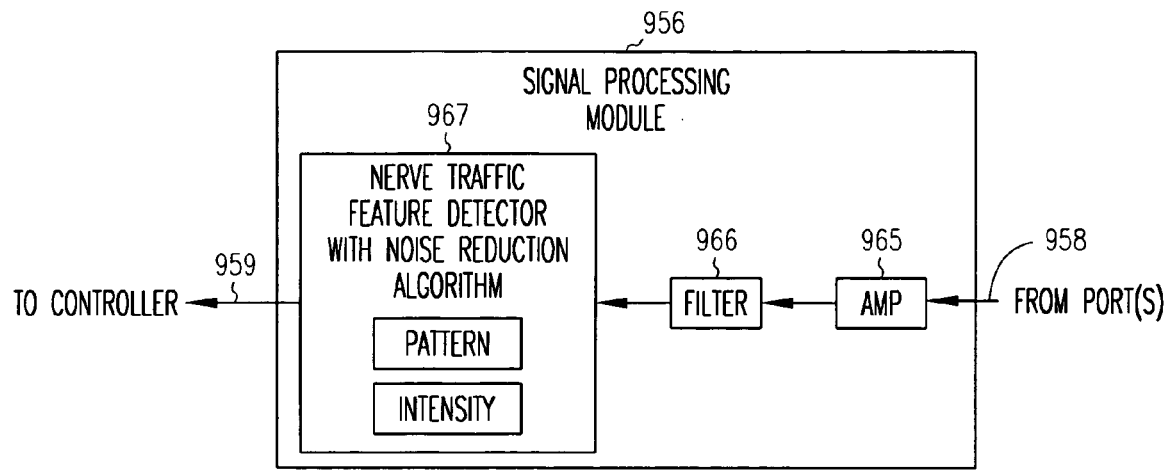
FIG. 9 illustrates a signal processing module, such as shown in the neural stimulators of FIGS. 7A-7C, according to various embodiments of the present subject matter.

FIG. 9 illustrates a signal processing module, such as shown in the neural stimulators of FIGS. 7A-7C, according to various embodiments of the present subject matter. The illustrated signal processing module 956 is adapted to receive a nerve traffic signal via path 958 and port(s) from lead(s) and to provide a signal indicative of the nerve traffic via path 959 to the controller. Various embodiments include an amplifier 965 and filter 966 adapted to process the nerve activity into a signal conditioned for discrimination or other processing. Various amplifier embodiments provide a gain within a range of approximately 1,000 to 99,000. Various filter embodiments pass frequencies in a range from approximately 30 Hz to approximately 3,000 Hz. The illustrated signal processing module further includes a nerve traffic feature detector 967, also referred to as a discriminator, to process the amplified and filtered signal to provide a signal indicative of the nerve traffic to the controller. Various embodiments implement a noise reduction algorithm, such as a wavelet transformation, for use in discriminating the signal. Various embodiments of the nerve traffic feature detector discriminate a nerve traffic pattern feature and/or a nerve traffic intensity feature; and send these signals to the controller for use to guide the neural stimulation.

Figure 10:
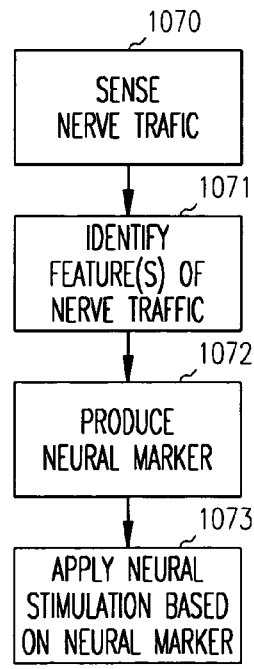
FIG. 10 illustrates method for closed-loop stimulation, according to various embodiments of the present subject matter.

FIG. 10 illustrates method for closed-loop stimulation, according to various embodiments of the present subject matter. At 1070, nerve traffic is sensed. At 1071, one or more features of the nerve traffic is identified. Various embodiments for identifying the feature(s) of the nerve traffic include implementing a noise reduction algorithm, such as a wavelet transformation. Examples of identified features include the pattern and intensity of the nerve traffic. In various embodiments, discriminating the signal to identify features of the nerve traffic signal includes rectifying and applying a threshold to the nerve traffic signal. In various embodiments, the discriminated signal is integrated using, for example, an R-C Integrator 0.1 sec, to obtain a value for the nerve traffic activity over a 100 millisecond period of time. In various embodiments, discriminating the signal to identify features of the nerve traffic signal includes correlating the signal to an event, such as an applied therapy or a sensed event. At 1072, a neural marker is produced. The neural marker includes information regarding the features of the nerve traffic signal identified at 1071. Examples of such information include a time stamp and label. At 1073, neural stimulation is applied based on the neural marker produced at 1072. In various embodiments, a controller implements a stimulation protocol to change at least one parameter, such as duration, amplitude and/or frequency, of the stimulation signal. Another embodiment displays the neural marker in place of applying the neural stimulation based on the neural marker.

CRM Systems with Neural Traffic Feedback

Various embodiments include CRM systems with neural traffic feedback. The lead is adapted to be connected to a device, such as an implantable CRM device. The device processes the nerve signal with appropriate amplification and filtering for the low amplitude and high noise level associated with the nerve signal. Various embodiments provide a signal processing module that can include a wavelet transformation or other noise reduction algorithm. Recorded nerve traffic is processed with a detection algorithm adapted to identify the features of the signal, such as the pattern and intensity of the nerve traffic. The signal features are used to determine desired neural stimulation parameters, such as duration, frequency and amplitude. Leads can be placed in a number of appropriate neural stimulation and neural sensing locations to perform baroreflex or other therapy.

Various embodiments of the present subject matter include stand-alone implantable CRM systems, and include implantable devices that have integrated NS and CRM components, and include systems with at least one implantable NS device and an implantable CRM device capable of communicating with each other. Some embodiments of the NS and CRM devices directly communicate with each other wirelessly, some embodiments communicate through a wire lead connecting the implantable devices, and some embodiments independently communicate with an external device that functions as an intermediary to provide communication between the NS and CRM devices. Although implantable systems are illustrated and discussed, various aspects and embodiments of the present subject matter can be implemented in external devices.

Examples of CRM devices include implantable pacemakers, implantable cardiac defibrillators (ICDs), implantable devices capable of performing pacing and defibrillating functions, and CRT devices. Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output. Some embodiments provide neural stimulation to treat hypertension. CRM functions can be improved by sensing neural activity to provide a input or feedback for the CRM functions. For example, various embodiments record the nerve activity in the cardiac fat pads and use the sensed nerve activity to control the CRM functions. For example, various embodiments sense AV node activity to determine an intrinsic AV delay, allowing the CRM device to use the determined intrinsic AV delay to appropriately time pacing pulses.

Figure 11:
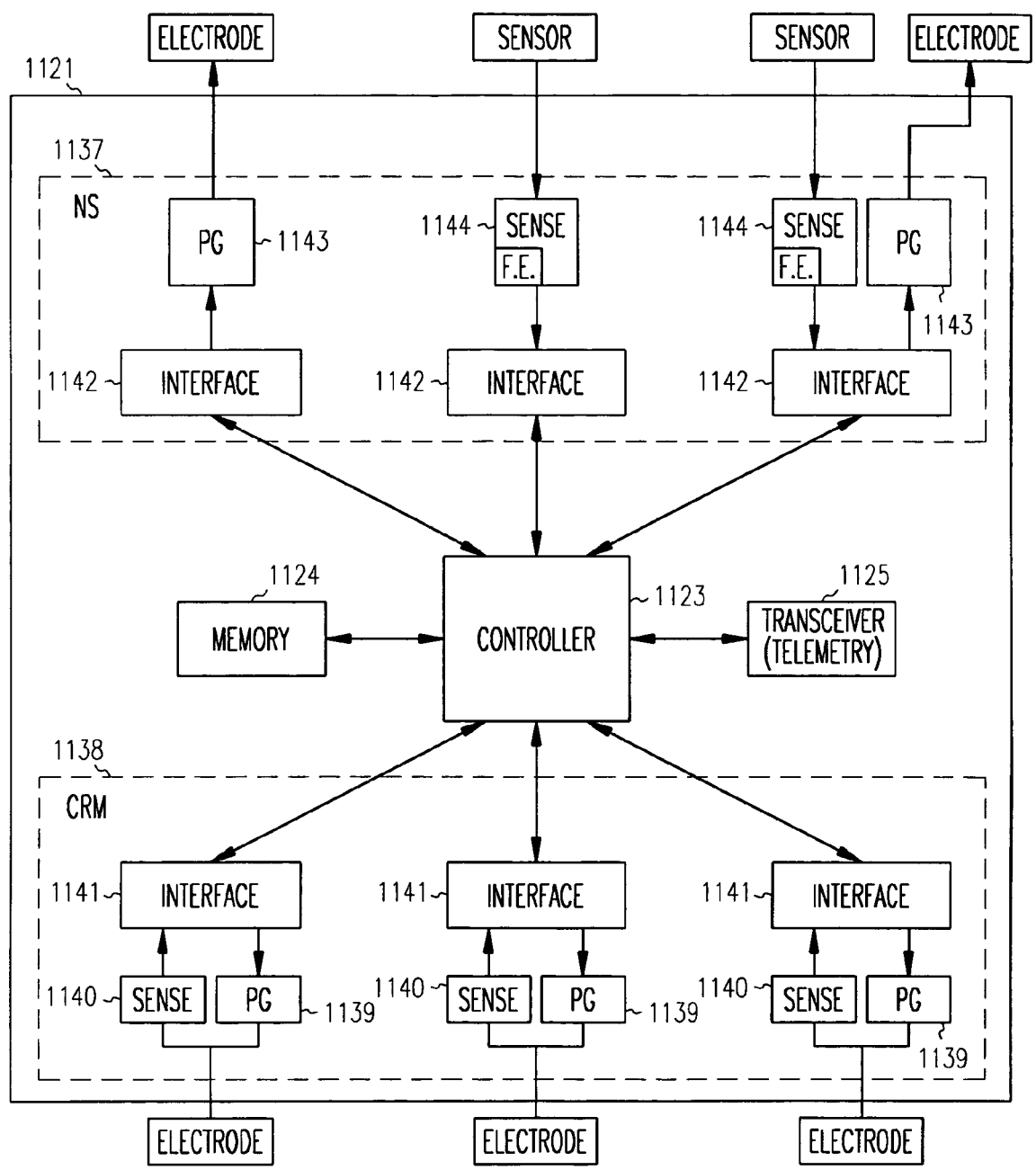
FIG. 11 illustrates an implantable medical device (IMD) such as shown in FIG. 3 having a neural stimulator (NS) component and cardiac rhythm management (CRM) component, according to various embodiments of the present subject matter.

FIG. 11 illustrates an implantable medical device (IMD) such as shown at 321 in FIG. 3 having a neural stimulator (NS) component and cardiac rhythm management (CRM) component, according to various embodiments of the present subject matter. Embodiments includes an IMD to delivery CRM therapy, an IMD to deliver neurostimulation therapy, an IMD to deliver drug therapy, and an IMD to deliver various combinations of CRM, neurostimulation and drug therapies. The illustrated device 1121 includes a controller 1123 and a memory 1124. According to various embodiments, the controller 1123 includes hardware, software, or a combination of hardware and software to perform the neural stimulation and CRM functions. Examples of CRM functions include, for example, pacing, defibrillating, and CRT functions. For example, the programmed therapy applications discussed in this disclosure are capable of being stored as computer-readable instructions embodied in memory and executed by a processor. According to various embodiments, the controller 1123 includes a processor to execute instructions embedded in memory to perform the CRM functions and neural sensing functions. Some embodiments further include neural stimulation functions. The illustrated device 1121 further includes a transceiver 1125 and associated circuitry for use to communicate with a programmer or another external or internal device. Various embodiments include a telemetry coil.

The CRM therapy section 1138 includes components, under the control of the controller, to stimulate a heart and/or sense cardiac signals using one or more electrodes. The CRM therapy section includes a pulse generator 1139 for use to provide an electrical signal through electrodes to stimulate a heart, and further includes sense circuitry 1140 to detect and process sensed cardiac signals or otherwise detect pulsatile parameters according to the present subject matter. An interface 1141 is generally illustrated for use to communicate between the controller 1123 and the pulse generator 1139 and sense circuitry 1140. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 1137 includes components, under the control of the controller, to sense nerve traffic, such as ANS parameters associated with nerve activity, and in some embodiments to stimulate nerves and/or to sense surrogates of ANS parameters such as blood pressure and respiration. Examples of NS therapy include, but are not limited to, therapies to treat hypertension, epilepsy, obesity and breathing disorders. Three interfaces 1142 are illustrated. However, the present subject matter is not limited to a particular number interfaces, or to any particular stimulating or sensing functions. Pulse generators 1143 are used to provide electrical pulses to an electrode for use to stimulate a site, such as a baroreceptor site to achieve a baroreflex response or a chemoreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 1144 are used to detect and process signals from a sensor, such as a sensor of nerve activity. Various embodiments further include sensors of pulsatile parameters, blood pressure, respiration, and the like. The illustrated sense circuits 1144 include a feature extractor (F.E.), such as illustrated at 431 in FIG. 4. The interfaces 1142 are generally illustrated for use to communicate between the controller 1123 and the pulse generator 1143 and sense circuitry 1144. Each interface, for example, may be used to control a separate lead. Other configurations are possible. For example, interface functions can be multiplexed to control a number of leads. Embodiments of the CRM therapy section modify therapy based on data received from the NS therapy section, such as nerve traffic data. Some embodiments further modify CRM therapy based on other parameters such as mean arterial pressure, systolic and diastolic pressure, and baroreflex stimulation rate. Embodiments of the NS therapy section modify therapy based on nerve traffic data.

According to various embodiments, the lead(s) and the electrode(s) on the leads are physically arranged with respect to the heart in a fashion that enables the electrodes to properly transmit pacing pulses and sense intrinsic signals from the heart, and with respect to baroreceptors, such as nerve endings and nerve trunks, to sense nerve traffic and in some embodiments to stimulate the baroreflex. As there may be a number of leads and a number of electrodes per lead, the configuration can be programmed to use a particular electrode or electrodes.

Figure 12:
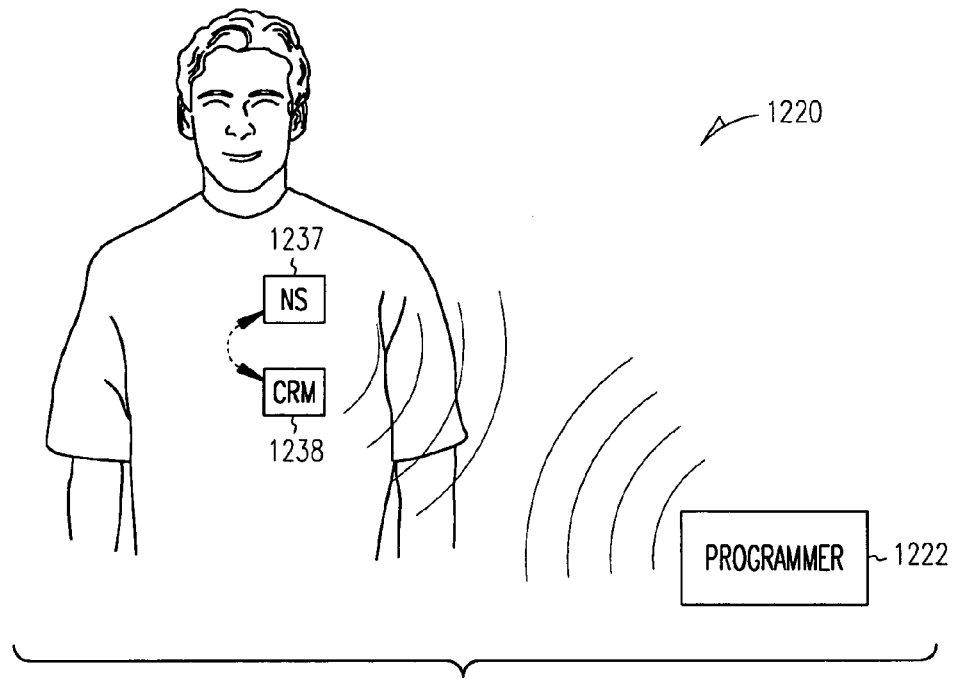
FIG. 12 illustrates a system including a programmer, an implantable neural stimulator (NS) device and an implantable cardiac rhythm management (CRM) device, according to various embodiments of the present subject matter.

FIG. 12 illustrates a system 1220 including a programmer 1222, an implantable neural stimulator (NS) device 1237 and an implantable cardiac rhythm management (CRM) device 1238, according to various embodiments of the present subject matter. Various aspects involve a method for communicating between an NS device 1237, such as an AHT device, and a CRM device 1238 or other cardiac stimulator. In various embodiments, this communication allows one of the devices 1237 or 1238 to deliver more appropriate therapy (i.e. more appropriate NS therapy or CRM therapy) based on data received from the other device. Some embodiments provide on-demand communications. In various embodiments, this communication allows each of the devices 1237 and 1238 to deliver more appropriate therapy (i.e. more appropriate NS therapy and CRM therapy) based on data received from the other device. The illustrated NS device 1237 and the CRM device 1238 are capable of wirelessly communicating with each other, and the programmer is capable of wirelessly communicating with at least one of the NS and the CRM devices 1237 and 1238. For example, various embodiments use telemetry coils to wirelessly communicate data and instructions to each other. In other embodiments, communication of data and/or energy is by ultrasonic means.

The NS device 1237 senses ANS activity, and in some embodiments, the NS device also stimulates the baroreflex to provide NS therapy. The CRM device 1238 includes cardiac stimulation capabilities, such as pacing and/or defibrillating capabilities. Some CRM device embodiments provide CRT functions. Rather than providing wireless communication between the NS and CRM devices 1237 and 1238, various embodiments provide a communication cable or wire, such as an intravenously-fed lead, for use to communicate between the NS device 1237 and the CRM device 1238.

Figure 13:
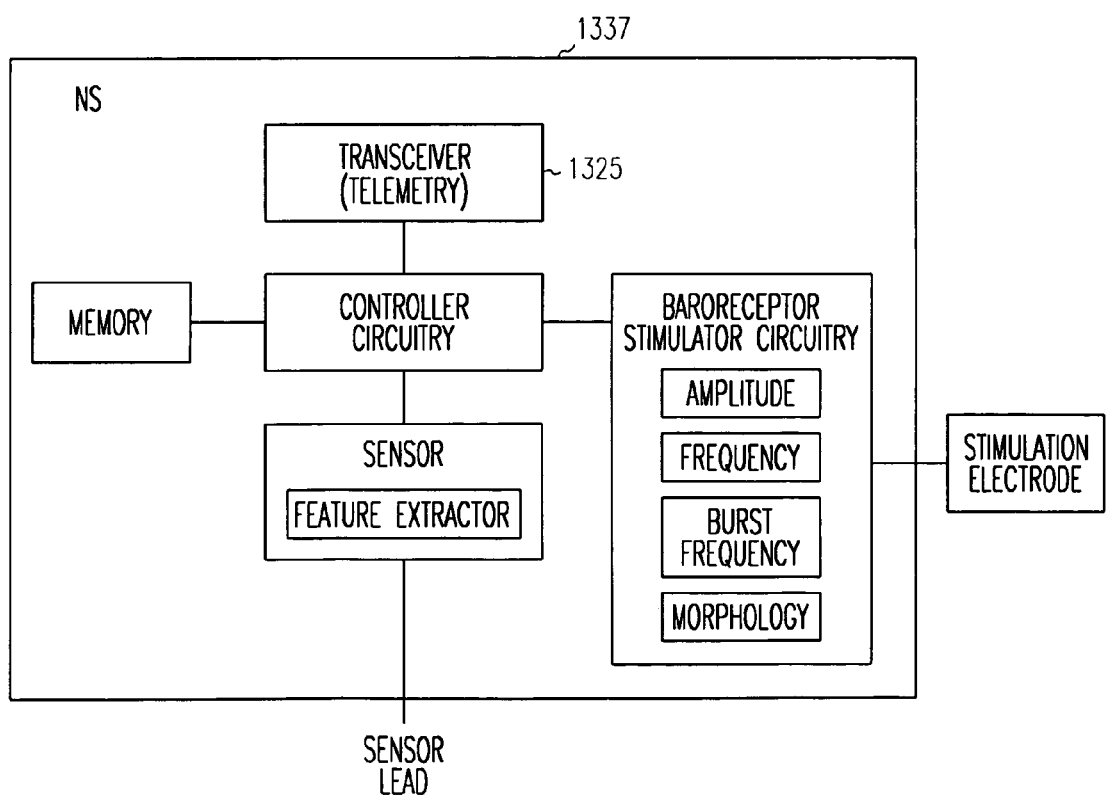
FIG. 13 illustrates an implantable neural stimulator (NS) device such as shown in the system of FIG. 12, according to various embodiments of the present subject matter.
Figure 14:
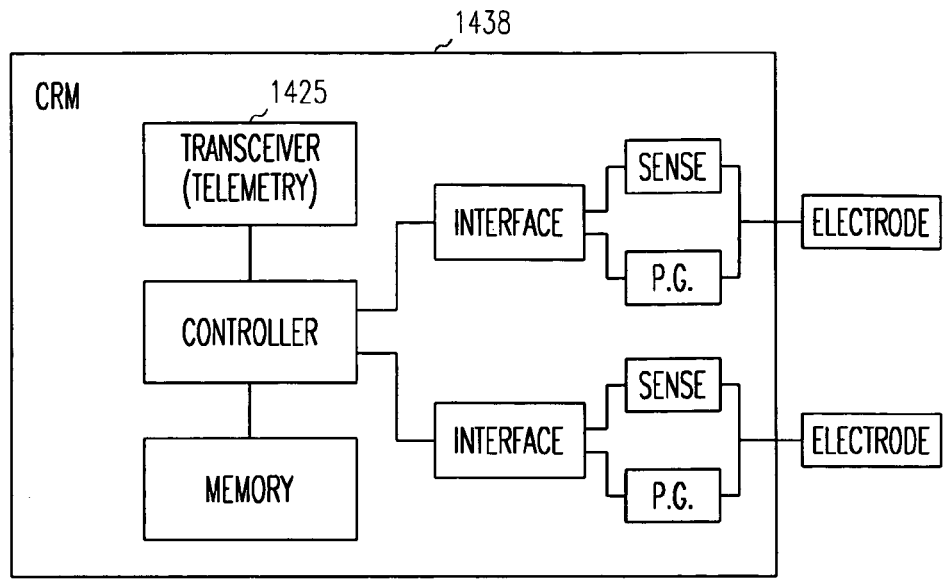
FIG. 14 illustrates an implantable cardiac rhythm management (CRM) device such as shown in the system of FIG. 12, according to various embodiments of the present subject matter.

FIG. 13 illustrates an implantable neural stimulator (NS) device 1337 such as shown at 1237 in the system of FIG. 12, according to various embodiments of the present subject matter. In various embodiments, an implantable nerve traffic sensor without neural stimulation capabilities is substituted for the device 1337. FIG. 14 illustrates an implantable cardiac rhythm management (CRM) device 1438 such as shown at 1238 in the system of FIG. 12, according to various embodiments of the present subject matter. Functions of the components for the NS device 1337 were previously discussed, and functions of the components for the CRM device 1438 were previously discussed. In the interest of brevity, these discussions with respect to the NS and CRM functions are not repeated here. Various embodiments of the NS and CRM devices include wireless transceivers 1325 and 1425, respectively, to wirelessly communicate with each other. Various embodiments of the NS and CRM devices include a telemetry coil or ultrasonic transducer to wirelessly communicate with each other.

The CRM device modifies therapy based on data received from the NS device, such as sensed nerve traffic. A feature extractor extracts features of the sensed nerve traffic and provides neural markers, which are used to control therapy in some embodiments. Various CRM device embodiments further modify therapy based on other data received from the NS device, such as mean arterial pressure, systolic and diastolic pressure, and baroreceptors stimulation rate. Various CRM device embodiments perform CRT functions. Various NS device embodiments are adapted to modify therapy based on electrophysiological parameters received from the CRM device such as heart rate, minute ventilation, atrial activation, ventricular activation, and cardiac events. The functionality of two or more implanted devices is enhanced by providing communication capabilities between or among the implanted devices. In various embodiments, the functionality is further enhanced by designing the devices to wirelessly communicate with each other.

Figure 15:
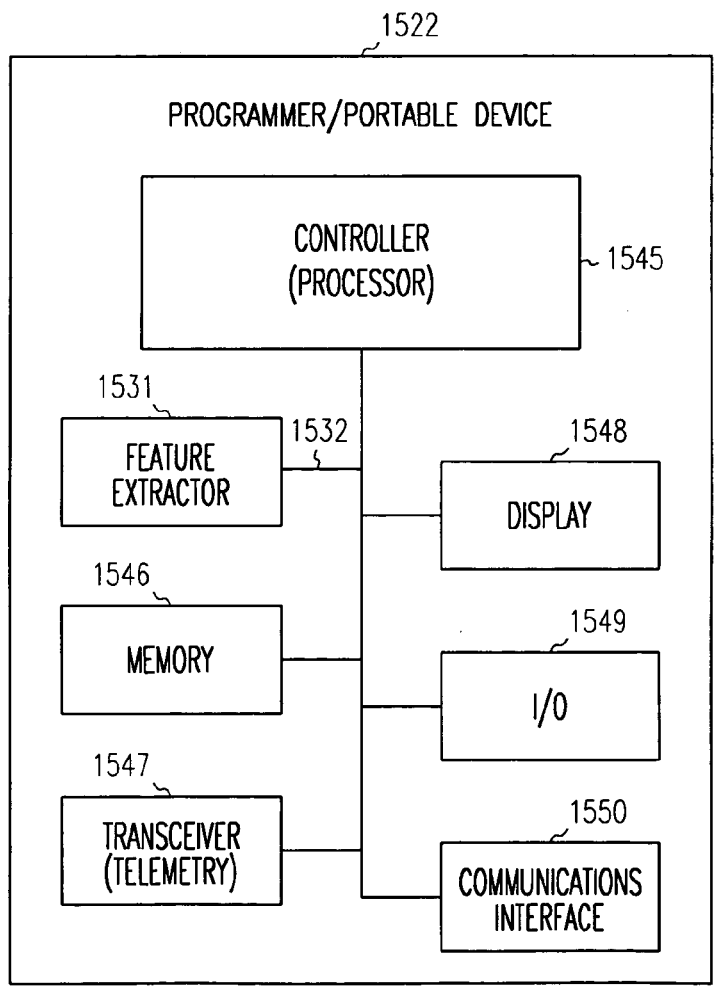
FIG. 15 illustrates a programmer, such as the programmer illustrated in the system of FIG. 12, or other external device to communicate with the implantable medical device(s), according to various embodiments of the present subject matter.

FIG. 15 illustrates a programmer 1522, such as the programmer 1222 illustrated in the system of FIG. 12, or other external device to communicate with the implantable medical device(s), according to various embodiments of the present subject matter. An example of another external device includes Personal Digital Assistants (PDAs) or personal laptop and desktop computers in an Advanced Patient Management (APM) system. The illustrated device 1522 includes controller circuitry 1545 and a memory 1546. The controller circuitry 1545 is capable of being implemented using hardware, software, and combinations of hardware and software. For example, according to various embodiments, the controller circuitry 1545 includes a processor to perform instructions embedded in the memory 1546 to perform a number of functions, including communicating data and/or programming instructions to the implantable devices. The illustrated device 1522 further includes a transceiver 1547 and associated circuitry for use to communicate with an implantable device. Various embodiments have wireless communication capabilities. For example, various embodiments of the transceiver 1547 and associated circuitry include a telemetry coil for use to wirelessly communicate with an implantable device. The illustrated device 1522 further includes a display 1548, input/output (I/O) devices 1549 such as a keyboard or mouse/pointer, and a communications interface 1550 for use to communicate with other devices, such as over a communication network. The illustrated device 1522 also includes a feature extractor 1531, such as illustrated at 431 in FIG. 4. The feature extractor 1531 receives neural waveforms through a port 1532, and can process neural waveforms received through transceiver 1547 from the implantable device, or can process neural waveforms stored in memory 1546.

The above-described functions of a system, whether implemented in two separate and distinct implantable devices or integrated as components into one or more implantable devices, includes, but is not limited to, processes for monitoring nerve traffic as part of a closed-loop neural stimulation system to continuously deliver appropriate neural stimulation. Processes can be performed by a processor executing computer-readable instructions embedded in memory, for example.

The present subject matter provides CRM therapy with nerve traffic feedback using lead(s) that can be used to detect and monitor nerve traffic. The lead is adapted to be connected to a device, such as an implantable CRM device. The device processes the nerve signal with appropriate amplification and filtering for the low amplitude and high noise level associated with the nerve signal. Various embodiments provide a signal processing module that can include a wavelet transformation or other noise reduction algorithm. Recorded nerve traffic is processed with a detection algorithm adapted to identify the features of the signal, such as the pattern and intensity of the nerve traffic. The signal features are used to determine desired parameters of CRM therapy.

A lead to sense nerve traffic can be placed in a number of appropriate locations. For example, various lead embodiments are expandable, and are adapted to be placed in the pulmonary artery in the proximity of a high concentration of baroreceptors. Various lead embodiments are adapted to sense nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. Other leads can be placed in other neural sensing locations for use in monitoring nerve traffic to provide feedback for CRM therapy. Various device embodiments monitor and record autonomic nerve traffic data as part of an APM system.

Figure 16:
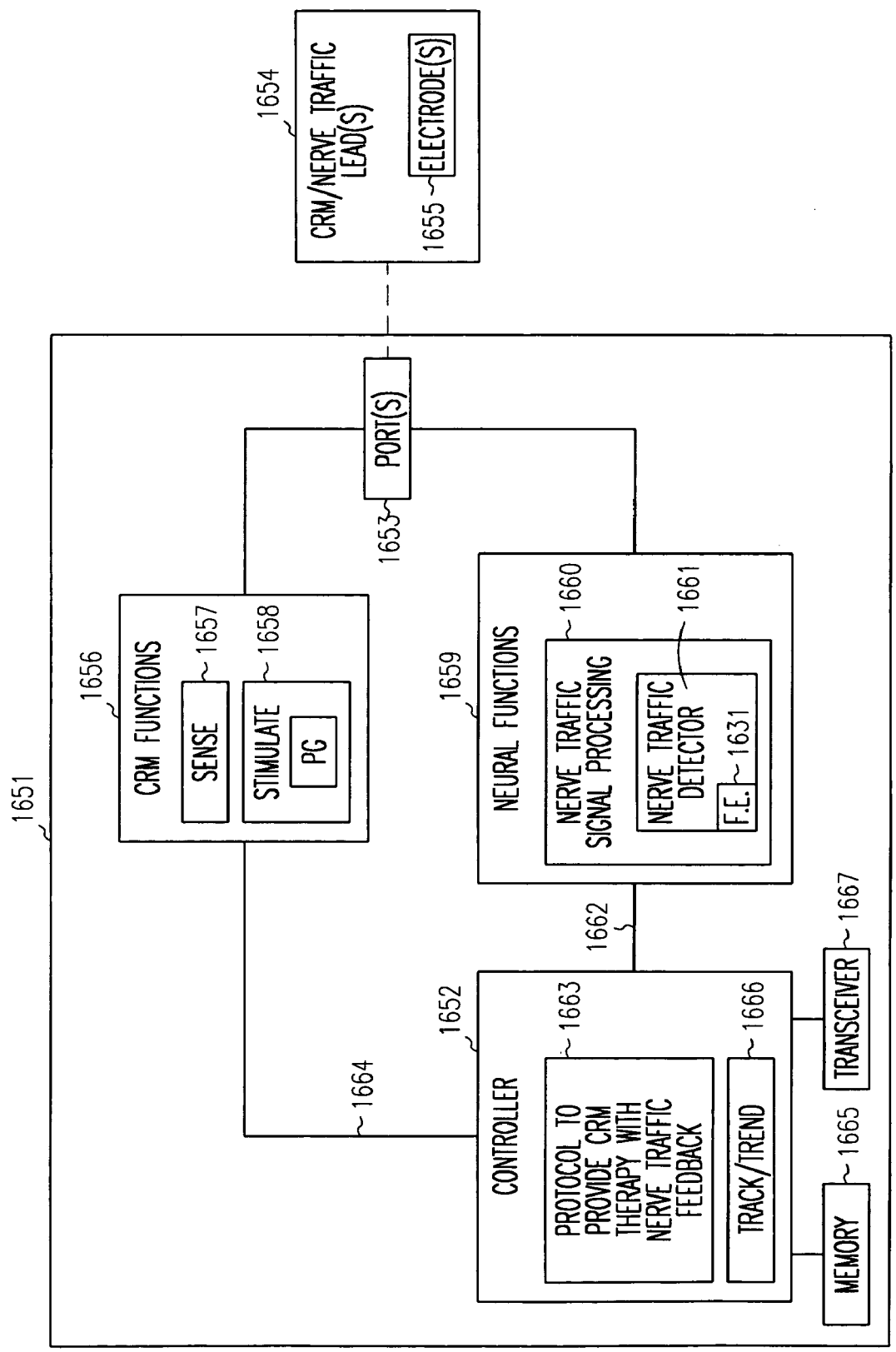
FIG. 16 illustrates an IMD device adapted to provide CRM therapy with nerve traffic feedback, according to various embodiments of the present subject matter.

FIG. 16 illustrates an IMD device adapted to provide CRM therapy with nerve traffic feedback, according to various embodiments of the present subject matter. The illustrated device 1651 includes a controller 1652 and at least one port 1653. Each port is adapted to be connected to a lead 1654, the connection being illustrated by the dotted line. Each lead includes at least one electrode 1655. CRM therapy and nerve traffic sensing are performed using one or more leads. For example, various embodiments use the same lead to apply stimulation signals to capture cardiac tissue for pacing or defibrillation, to sense electrogram signals from the heart, and to sense nerve traffic. These functions are capable of being performed using the same electrode on the lead, to using different electrodes on the same lead, or using electrodes on different leads. Various embodiments use different electrodes to sense nerve traffic and to perform the CRM therapy.

The illustrated IMD device 1651 includes a CRM functions module 1656 to perform CRM functions, including sense functions 1657 and stimulate functions 1658. The CRM function module is illustrated between the port(s) and the controller.

The illustrated IMD device 1651 includes a neural functions module 1659 to perform neural functions, including a module 1660 to process nerve traffic signals from at least one electrode on at least one lead. The neural functions module is illustrated between the controller and the port(s). Various embodiments of the neural functions module 1659 include a nerve traffic detector 1661 to detect a nerve traffic parameter corresponding to a nerve traffic pattern, various embodiments detect a nerve traffic parameter corresponding to nerve traffic intensity, and various embodiments detect a nerve traffic parameter corresponding to a nerve traffic pattern and a nerve traffic intensity. The illustrated nerve traffic detector 1661 includes a feature extractor 1631, such as the feature extractor 431 in FIG. 4.

The controller 1652 is adapted to receive a signal indicative of nerve traffic via signal path 1662 from the neural function module 1659, to implement a protocol 1663 to provide CRM therapy with nerve traffic feedback, and to control the CRM functions module 1656 via signal path 1664. Thus, according to various embodiments, for example, the controller is adapted to adjust CRM therapy based on a detected nerve traffic pattern and/or a detected nerve intensity.

The illustrated device 1651 further includes a memory 1665. In various embodiments, the controller is adapted to store nerve traffic data in the memory, and to track or trend the nerve traffic data using the track/trend module 1666 to further guide the CRM therapy. The illustrated device 1651 further includes a transceiver 1667 to communicate with the controller for use to communicate with another IMD, a programmer, or an advanced patient management (APM) device.

Functions performed by the illustrated modules can be implemented using hardware, software, and a combination of software and hardware. Logical changes can be made such that the functions can be logically grouped in other modules or to form different modules. For example, in various embodiments, the controller includes the hardware and/or software to detect the nerve traffic.

Figure 17:
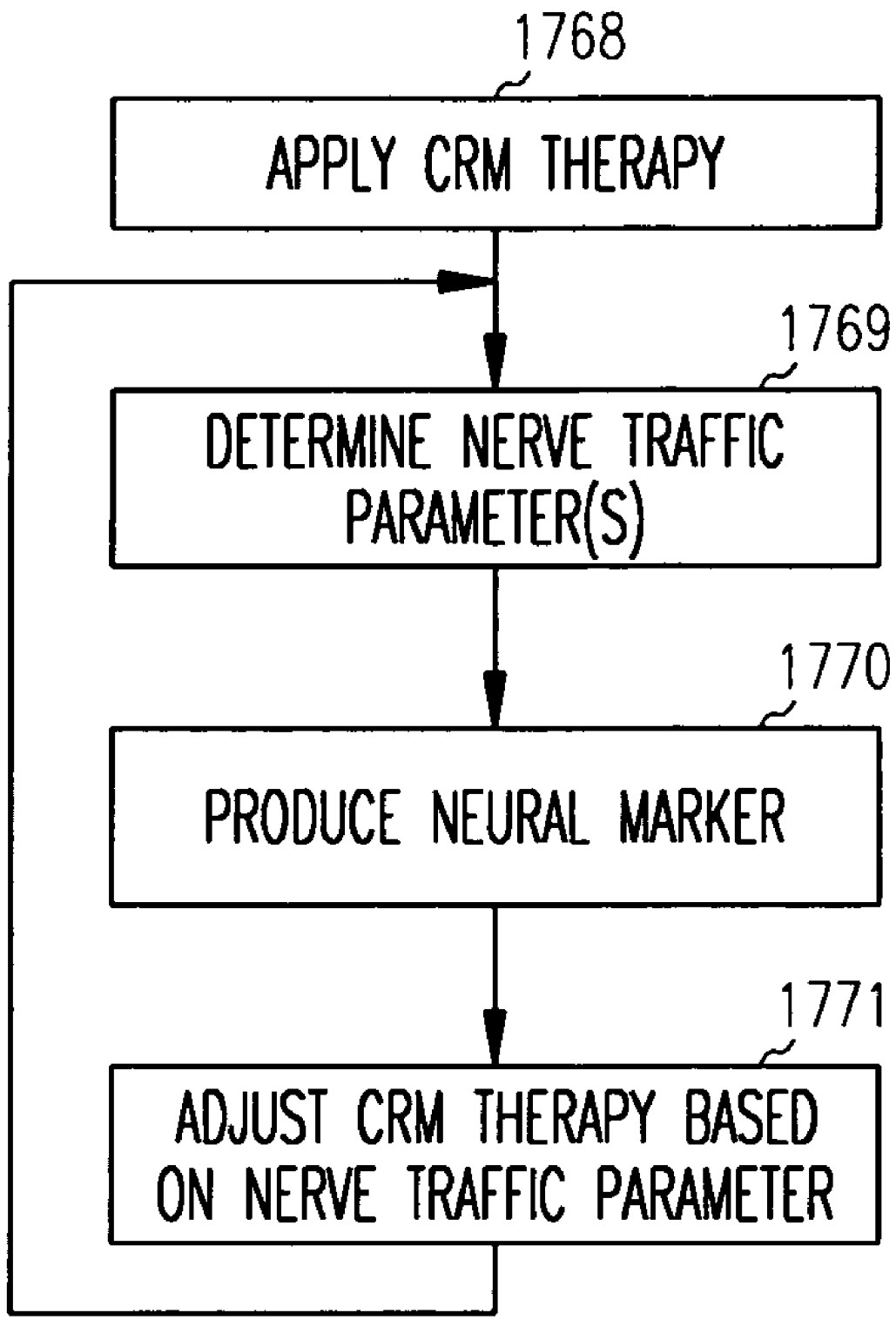
FIG. 17 illustrates a method performed by the IMD device of FIG. 16, according to various embodiments of the present subject matter.

FIG. 17 illustrates a method performed by the IMD device of FIG. 16, according to various embodiments of the present subject matter. At 1768, CRM therapy is applied. For example, various embodiment apply the CRM therapy using the CRM function module 1656 under the control of the controller 1652, such as illustrated in FIG. 16. Various embodiments apply CRT as a CRM therapy. At 1769, at least one nerve traffic parameter is determined. For example, various embodiments determine the nerve traffic parameter using the neural functions module 1659, and provide a signal indicative of the at least one nerve traffic parameter via signal path 1662, such as illustrated in FIG. 16. At 1770, a neural marker is produced based on the nerve traffic parameter(s). The feature extractor 1631 of FIG. 16 is adapted to produce the neural marker. At 1771, the CRM therapy is adjusted based on the neural marker. The nerve traffic is affected by the applied CRM therapy, such that the sensed nerve traffic parameter provides a closed loop feedback for the CRM therapy. For example, various embodiments receive the neural marker indicative of the sensed nerve traffic at the controller 1652, which implements the protocol 1663 to adjust the CRM therapy based on the nerve traffic parameter.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter.

The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired CRM therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiments shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:
    sensing nerve traffic representative of autonomic nervous system (ANS) activity using an implantable medical device (IMD);
    extracting features from the sensed nerve traffic;
    creating ANS neural markers for the extracted features, the ANS neural markers including information for the ANS neural markers regarding the extracted features; and
    displaying a list of the ANS neural markers using an external device, including displaying both labels for the ANS neural markers and the information for the ANS neural markers in the list, wherein displaying the information for the ANS neural markers in the list includes displaying events correlated with the ANS neural markers in the list.

2. The method of claim 1, wherein extracting features includes filtering the sensed nerve traffic.

3. The method of claim 2, wherein filtering includes applying a wavelet transformation to the sensed nerve traffic.

4. The method of claim 2, wherein filtering includes applying a frequency-based filter to the sensed nerve traffic.

5. The method of claim 2, wherein filtering includes rectifying the sensed nerve traffic.

6. The method of claim 2, wherein filtering includes applying a moving window average to the sensed nerve traffic.

7. The method of claim 2, wherein filtering includes applying a logarithmic averaging to the sensed nerve traffic.

8. The method of claim 2, wherein filtering includes averaging repeated signals that are aligned to an index event.

9. The method of claim 1, wherein extracting features includes correlating the sensed nerve traffic to an event.

10. The method of claim 9, wherein the event includes an application of a therapy.

11. The method of claim 9, wherein the event includes a sensed event.

12. The method of claim 1, wherein extracting features includes comparing a parameter of the sensed nerve traffic to at least one programmable value.

13. The method of claim 1, wherein the information includes labels for the extracted features.

14. The method of claim 1, wherein the information includes time stamps for the extracted features.

15. The method of claim 1, wherein the information includes an indicator of a location for the ANS activity.

16. The method of claim 1, wherein the information includes an indicator of a neural pathway type.

17. The method of claim 1, wherein the information includes information regarding a correlated event.

18. The method of claim 1, wherein the information includes information regarding at least one parameter of the sensed nerve traffic representative of ANS activity.

19. The method of claim 1, further comprising automatically adjusting an applied therapy based on the neural marker using the IMD or using the external device to communicate to the IMD, wherein the IMD is configured to apply the therapy.

20. The method of claim 1, further comprising automatically providing status information for an applied therapy based on the ANS neural markers using the IMD or using the external device to communicate to the IMD, wherein the IMD is configured to apply the therapy.

21. The method of claim 20, wherein displaying the information for the ANS neural markers includes displaying information regarding correlated events associated with the sensed nerve traffic.

22. The method of claim 20, further comprising forming ANS neurograms from the sensed nerve traffic, wherein displaying the information for the ANS neural markers includes displaying a segment of each of the ANS neurograms for a time period determined by a time stamp of the ANS neural markers.

23. The method of claim 1, further comprising storing the neural markers in a memory, including automatically storing a neural marker in the memory in response to a trigger produced for at least one predetermined feature extracted from the sensed nerve traffic.

24. The method of claim 23, further comprising storing the neural markers in the memory in response to a user-initiated trigger.

25. The method of claim 1, further comprising forming ANS neurograms from the sensed nerve traffic, and displaying portions of the ANS neurograms with a representation identifying the ANS neural markers within the ANS neurograms.

26. The method of claim 25, further comprising selecting one of the ANS neural markers in the list to display portions of one of the ANS neurograms corresponding to the selected ANS neural markers.

27. The method of claim 25, further comprising using a time stamp for the ANS neural markers to determine ANS neurogram segments to be displayed.

28. The method of claim 1, wherein displaying the information for the ANS neural markers in the list includes displaying time information for the ANS neural markers in the list.

29. The method of claim 1, wherein displaying the information for the ANS neural markers in the list includes displaying locations of the sensed nerve traffic from which the ANS neural markers are created.

30. The method of claim 1, wherein displaying the information for the ANS neural markers in the list includes displaying neural pathway identifiers to identify neural pathways of the sensed nerve traffic.

31. The method of claim 30, wherein the neural pathway identifiers include an afferent pathway identifier or an efferent pathway identifier.

32. The method of claim 1, wherein displaying the information for the ANS neural markers in the list includes displaying amplitudes of signals corresponding to the sensed nerve traffic.

33. The method of claim 1, wherein displaying the information for the ANS neural markers in the list includes displaying frequencies of signals corresponding to the sensed nerve traffic.

34. A method, comprising:
sensing nerve traffic representative of autonomic nervous system (ANS) activity using an implantable medical device (IMD);
extracting features from the sensed nerve traffic;
creating ANS neural markers for the extracted features, the ANS neural markers including information for the ANS neural markers regarding the extracted features;
displaying a list of the ANS neural markers using an external device, including displaying both labels for the ANS neural markers and the information for the ANS neural markers in the list; and
automatically providing status information for an applied therapy based on the ANS neural markers using the IMD or using the external device to communicate to the IMD, wherein the IMD is configured to apply the therapy.

35. The method of claim 34, wherein displaying the information for the ANS neural markers includes displaying information regarding correlated events associated with the sensed nerve traffic.

36. The method of claim 34, further comprising forming ANS neurograms from the sensed nerve traffic, wherein displaying the information for the ANS neural markers includes displaying a segment of each of the ANS neurograms for a time period determined by a time stamp of the ANS neural markers.

37. A method, comprising:
sensing nerve traffic representative of autonomic nervous system (ANS) activity using an implantable medical device (IMD);
extracting features from the sensed nerve traffic;
creating ANS neural markers for the extracted features, the ANS neural markers including information for the ANS neural markers regarding the extracted features;
displaying a list of the ANS neural markers using an external device, including displaying both labels for the ANS neural markers and the information for the ANS neural markers in the list;
forming ANS neurograms from the sensed nerve traffic; and
displaying portions of the ANS neurograms with a representation identifying the ANS neural markers within the ANS neurograms.

38. The method of claim 37, further comprising selecting one of the ANS neural markers in the list to display portions of one of the ANS neurograms corresponding to the selected ANS neural marker.

39. The method of claim 37, further comprising using a time stamp for the ANS neural markers to determine ANS neurogram segments to be displayed.

40. A method, comprising:
sensing nerve traffic representative of autonomic nervous system (ANS) activity using an implantable medical device (IMD);

extracting features from the sensed nerve traffic;

creating ANS neural markers for the extracted features, the ANS neural markers including information for the ANS neural markers regarding the extracted features; and displaying a list of the ANS neural markers using an external device, including displaying both labels for the ANS neural markers and the information for the ANS neural markers in the list, wherein the information includes an indicator of a location for the ANS activity.

41. A method, comprising:

sensing nerve traffic representative of autonomic nervous system (ANS) activity using an implantable medical device (IMD);

extracting features from the sensed nerve traffic;

creating ANS neural markers for the extracted features, the ANS neural markers including information for the ANS neural markers regarding the extracted features; and displaying a list of the ANS neural markers using an external device, including displaying both labels for the ANS neural markers and the information for the ANS neural markers in the list, wherein the information includes an indicator of a neural pathway type.

42. A method, comprising:

sensing nerve traffic representative of autonomic nervous system (ANS) activity using an implantable medical device (IDM);

extracting features from the sensed nerve traffic;

creating ANS neural markers for the extracted features, the ANS neural markers including information for the ANS neural markers regarding the extracted features; and displaying a list of the ANS neural markers using an external device, including displaying both labels for the ANS neural markers and the information for the ANS neural markers in the list, wherein displaying the information for the ANS neural markers in the list includes displaying locations of the sensed nerve traffic from which the ANS neural markers are created.

43. A method, comprising:

sensing nerve traffic representative of autonomic nervous system (ANS) activity using an implantable medical device (IMD);

extracting features from the sensed nerve traffic;

creating ANS neural markers for the extracted features, the ANS neural markers including information for the ANS neural markers regarding the extracted features; and displaying a list of the ANS neural markers using an external device, including displaying both labels for the ANS neural markers and the information for the ANS neural markers in the list, wherein displaying the information for the ANS neural markers in the list includes displaying neural pathway identifiers to identify neural pathways of the sensed nerve traffic.

44. The method of claim 43, wherein the neural pathway identifiers include an afferent pathway identifier or an efferent pathway identifier.

45. A method, comprising:

sensing nerve traffic representative of autonomic nervous system (ANS) activity using an implantable medical device (IMD);

extracting features from the sensed nerve traffic;

creating ANS neural markers for the extracted features, the ANS neural markers including information for the ANS neural markers regarding the extracted features; and displaying a list of the ANS neural markers using an external device, including displaying both labels for the ANS neural markers and the information for the ANS neural markers in the list, wherein displaying the information for the ANS neural markers in the list includes displaying frequencies of signals corresponding to the sensed nerve traffic.

* * * * *

UNITED STATES PATENT AND TRADEMARK OFFICE
CERTIFICATE OF CORRECTION

| | | |
|---|---|---|
| PATENT NO. | : 7,640,057 B2 | Page 1 of 1 |
| APPLICATION NO. | : 11/113773 | |
| DATED | : December 29, 2009 | |
| INVENTOR(S) | : Imad Libbus et al. | |

It is certified that error appears in the above-identified patent and that said Letters Patent is hereby corrected as shown below:

In column 1, line 13, delete "10/922,319," and insert -- 10/992,319, --, therefor.

In column 23, line 27, in Claim 42, delete "(IDM);" and insert -- (IMD); --, therefor.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,640,057 B2 Page 1 of 1
APPLICATION NO. : 11/113773
DATED : December 29, 2009
INVENTOR(S) : Libbus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1222 days.

Signed and Sealed this

Twenty-first Day of December, 2010

David J. Kappos
*Director of the United States Patent and Trademark Office*